(12) United States Patent
Wang et al.

(10) Patent No.: US 7,820,174 B2
(45) Date of Patent: Oct. 26, 2010

(54) T CELL RECEPTORS AND RELATED MATERIALS AND METHODS OF USE

(75) Inventors: Qiong J. Wang, Reston, VA (US); Kenichi Hanada, Bethesda, MD (US); James C. Yang, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/196,833

(22) Filed: Aug. 22, 2008

(65) Prior Publication Data

US 2009/0042798 A1 Feb. 12, 2009

Related U.S. Application Data

(63) Continuation-in-part of application No. PCT/US2007/004454, filed on Feb. 22, 2007.

(60) Provisional application No. 60/776,194, filed on Feb. 24, 2006, provisional application No. 60/811,422, filed on Jun. 7, 2006.

(51) Int. Cl.
A61K 38/17 (2006.01)

(52) U.S. Cl. ..................... 424/192.1; 530/386

(58) Field of Classification Search ........................ None
See application file for complete search history.

(56) References Cited

U.S. PATENT DOCUMENTS 6,800,746 B2 10/2004 Xu et al.
2005/0009025 A1* 1/2005 Jakobsen et al. ............... 435/6
2006/0263334 A1 11/2006 Finn et al.

FOREIGN PATENT DOCUMENTS

| EP | 1 275 400 A1 | 1/2003 |
|---|---|---|
| WO | WO 01/73032 A2 | 10/2001 |
| WO | WO 03/000928 A2 | 1/2003 |
| WO | WO 2005/056595 A2 | 6/2005 |
| WO | WO 2007/100568 A2 | 9/2007 |

OTHER PUBLICATIONS

George Miklos, Nat Biotechnol. May 2005;23(5):535-7.*
Janeway et al., Immunobiology, 5th Ed., Garland Science, pp. 105-108; 262-263.*
Portolano et al., J Immunol. Feb. 1, 1993;150(3):880-7.*
Gras et al., Curr Opin Immunol. Feb. 2008;20(1):119-25.*
Boulter et al. Protein Eng. Sep. 2003;16(9):707-11.*
Alajez et al., Blood, 105 (12), 4583-4589 (2005).
Barnd et al., Proc. Natl. Acad. Sci. USA, 86, 7159-7163 (1989).
Choudhary et al., J. Immunol., 154, 3932-3940 (1995).
EBI Database Accession No. AAU69943 (2002).
Engels et al., Hum. Gene Ther., 16 (7), 800-802 (2005).
GenBank Accession No. AAB24537.1 (1993).
GenBank Accession No. AAB69013 (2002).
GenBank Accession No. AAC80217.1 (2005).
Hanada et al., Cancer Res., 61, 5511-5516 (2001).
Hanada et al., Nature, 427, 252-256 (2004).
Holoshitz et al., Curr. Topics in Microbio. and Immunol., 173, 167-172 (1991).
Itoh et al., J. Exp. Med., 168, 1419-1441 (1988).
Jantzer et al., Cancer Res., 58 (14), 3078-3086 (1998).
Kirri et al., J. Immunol., 21, 188-197 (1998).
Leroy et al., Am. J. Clin. Pathol., 118, 47-51 (2002) (Abstract).
Magarian-Blander et al., J. Immunol., 160, 3111-3120 (1998).
Morita et al., Reg. Immunol., 4 (4), 225-235 (1992).
Patel et al., J. Immunol., 139 (11), 3886-3895 (1987).
Schendel et al., J. Mol. Med., 75 (6), 400-413 (1997).
Thiele et al., Immunol. Today, 10, 375-381 (1989).
Wang et al., J. Immunother., 28 (6), 551-559 (2005).
EBI Database Accession No. AX658301, May 31, 2006.

* cited by examiner

*Primary Examiner*—Zachary Skelding
(74) *Attorney, Agent, or Firm*—Leydig, Voit & Mayer

(57) ABSTRACT

The invention provides an isolated or purified T cell receptor (TCR) having antigenic specificity for a cancer antigen, e.g., a renal cell carcinoma antigen, wherein the TCR recognizes the cancer antigen in a major histocompatibility complex (MHC)-independent manner. Also provided are related polypeptides, proteins, nucleic acids, recombinant expression vectors, isolated host cells, populations of cells, antibodies, or antigen binding portions thereof, and pharmaceutical compositions. The invention further provides a method of detecting the presence of cancer in a host and a method of treating or preventing cancer in a host using the inventive TCRs or related materials.

10 Claims, 24 Drawing Sheets

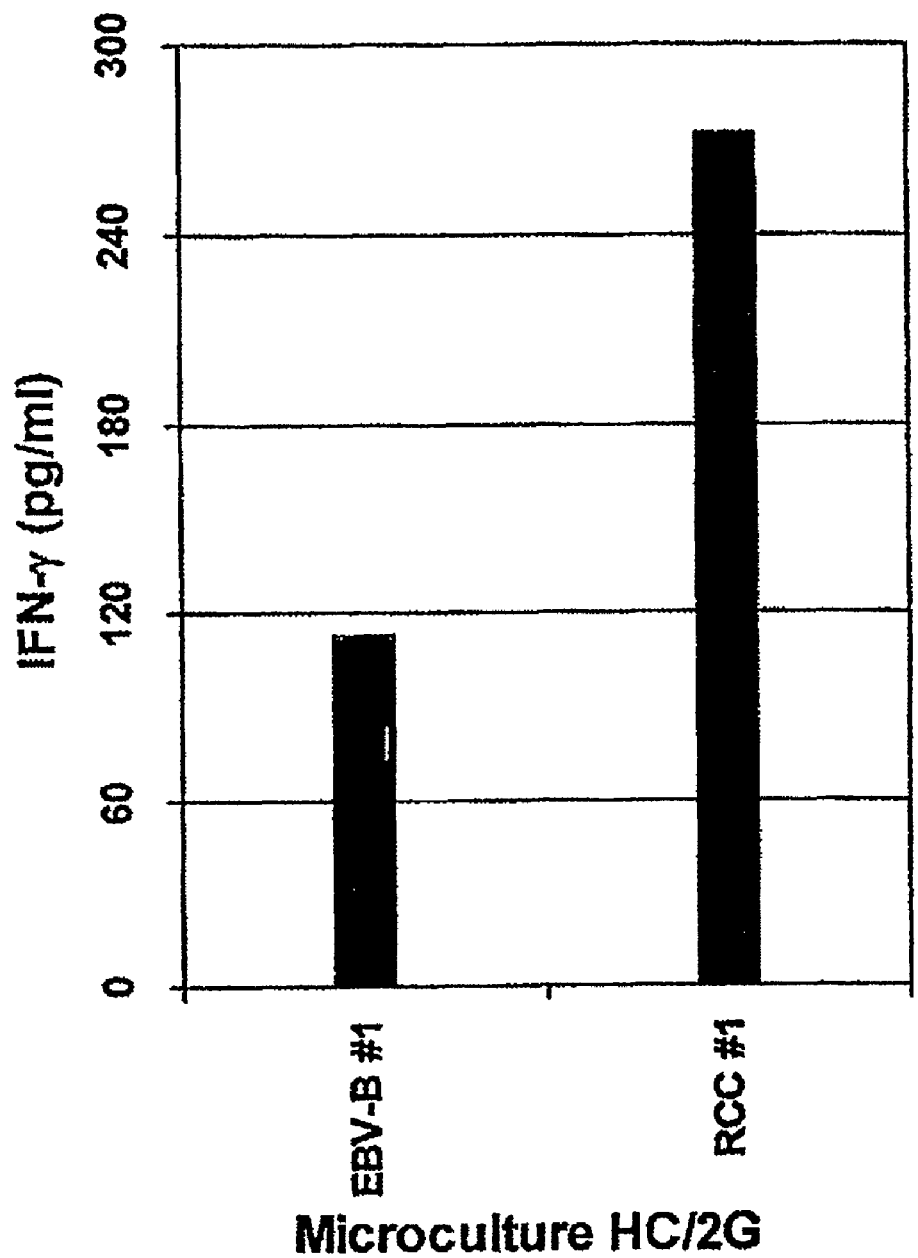

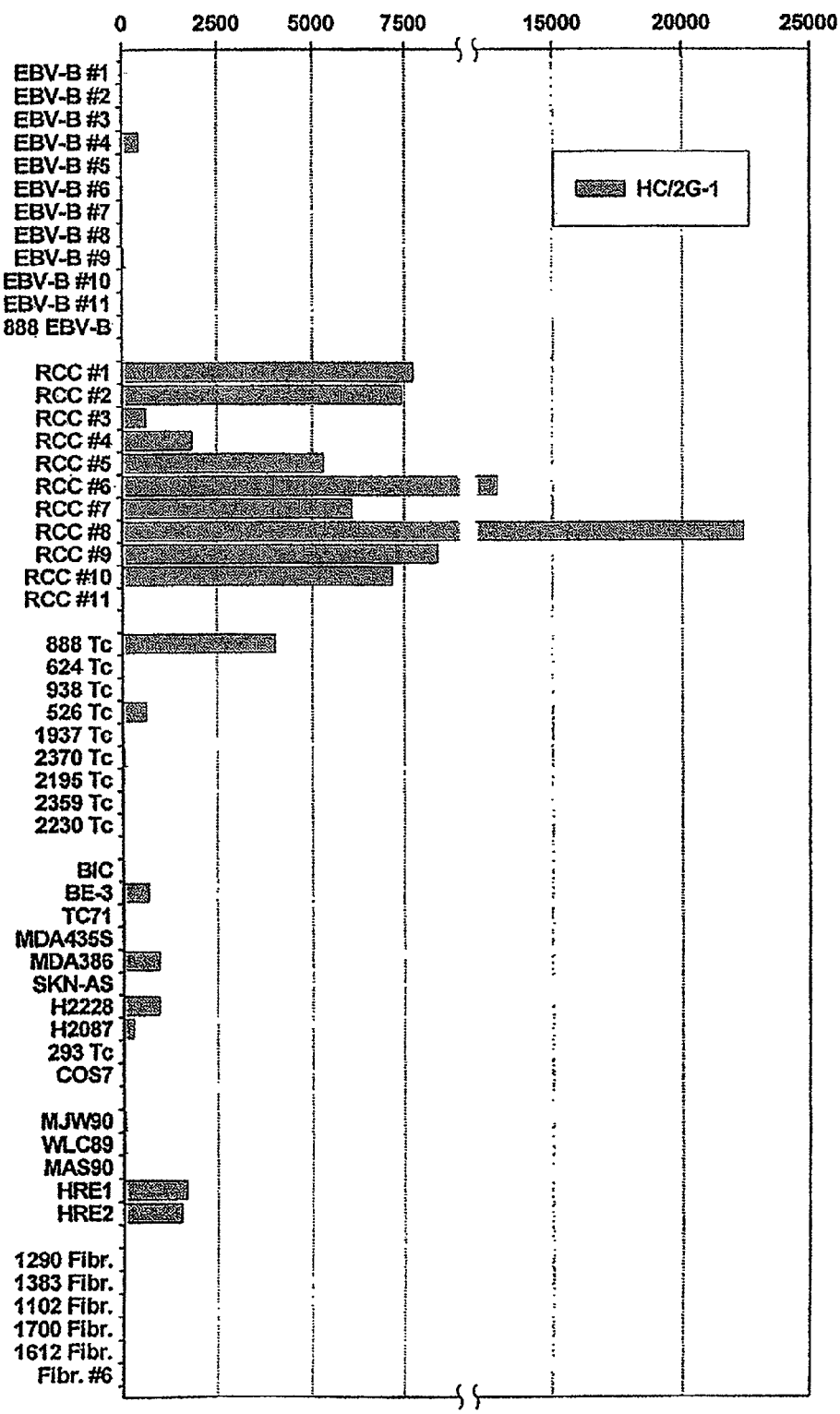

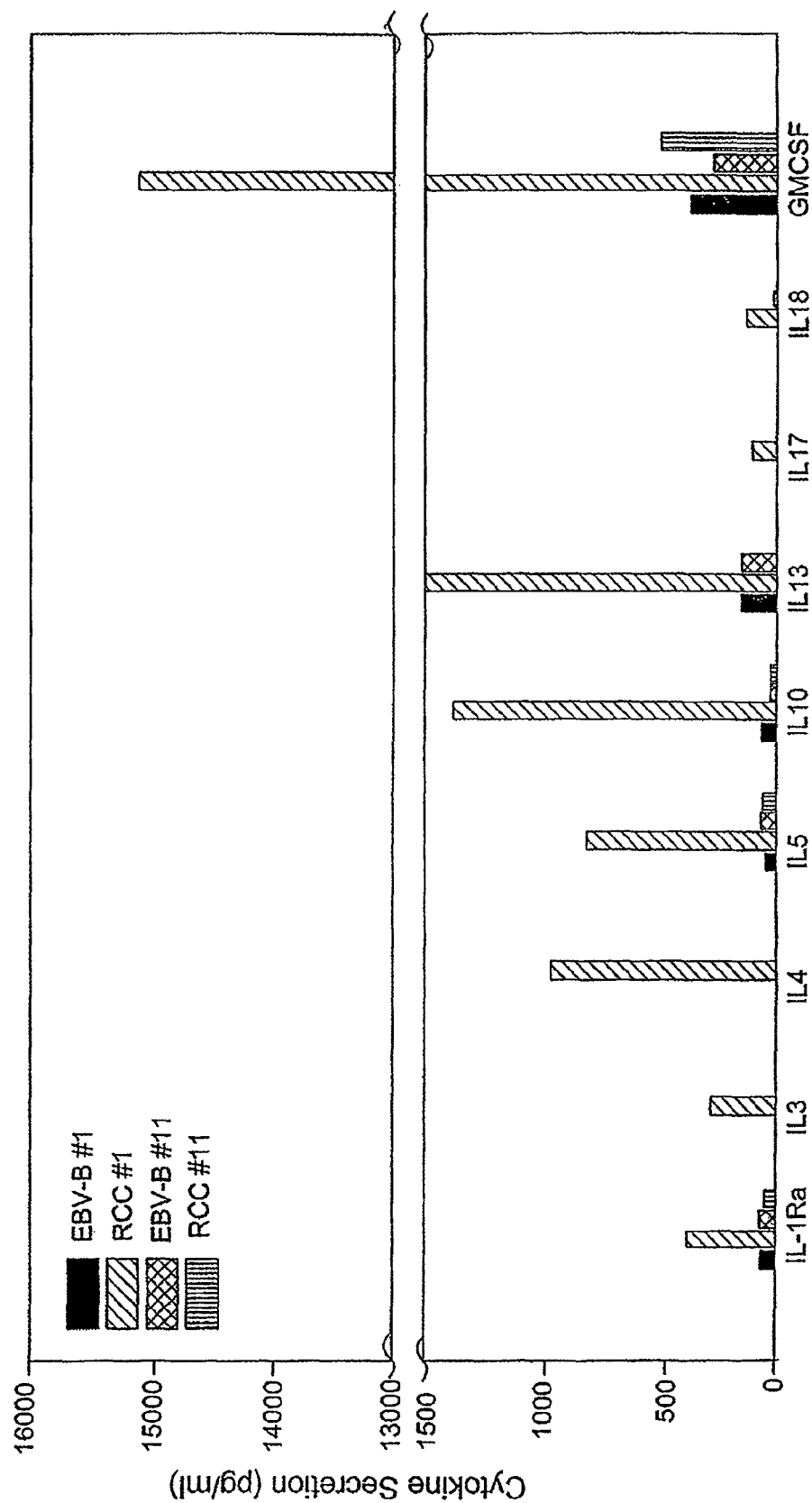

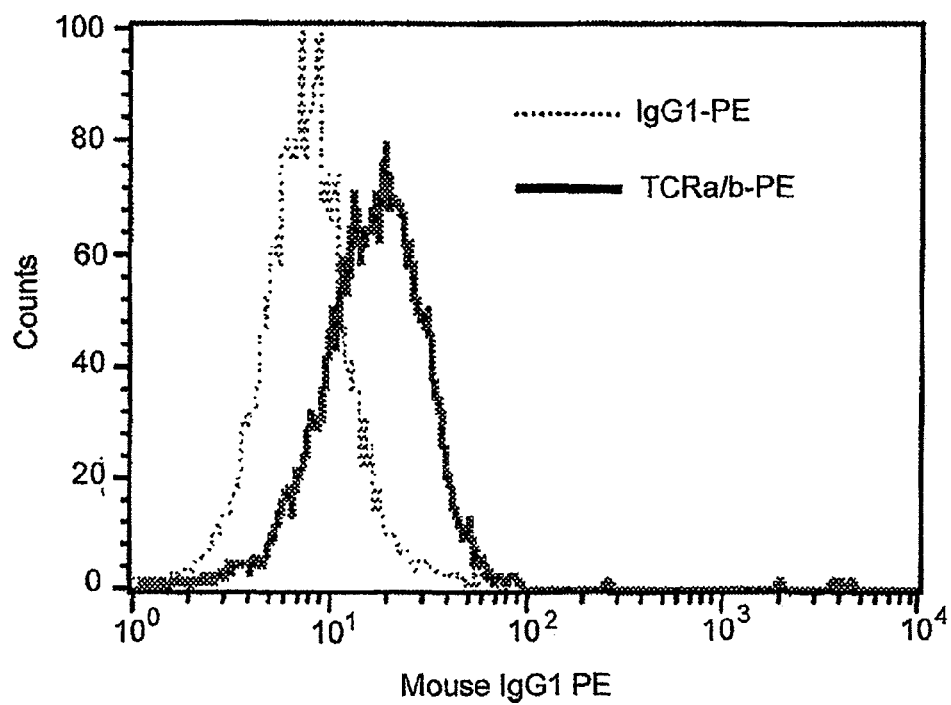

FIG. 3B
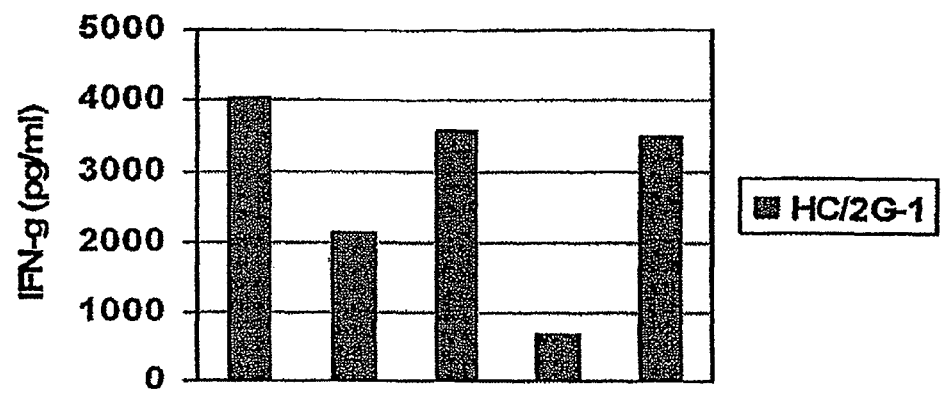
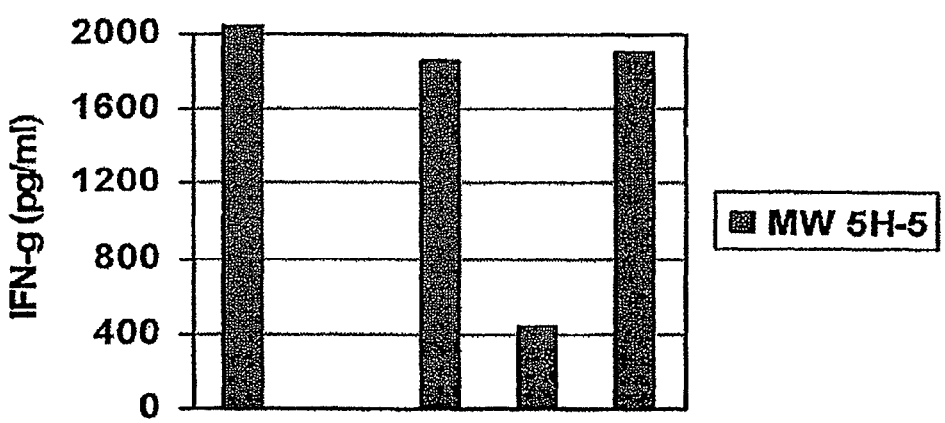
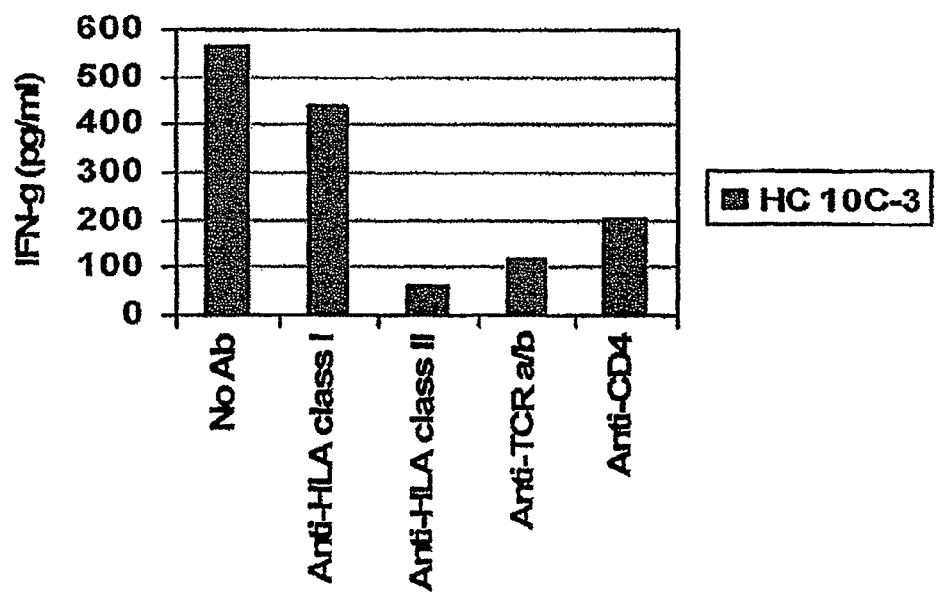

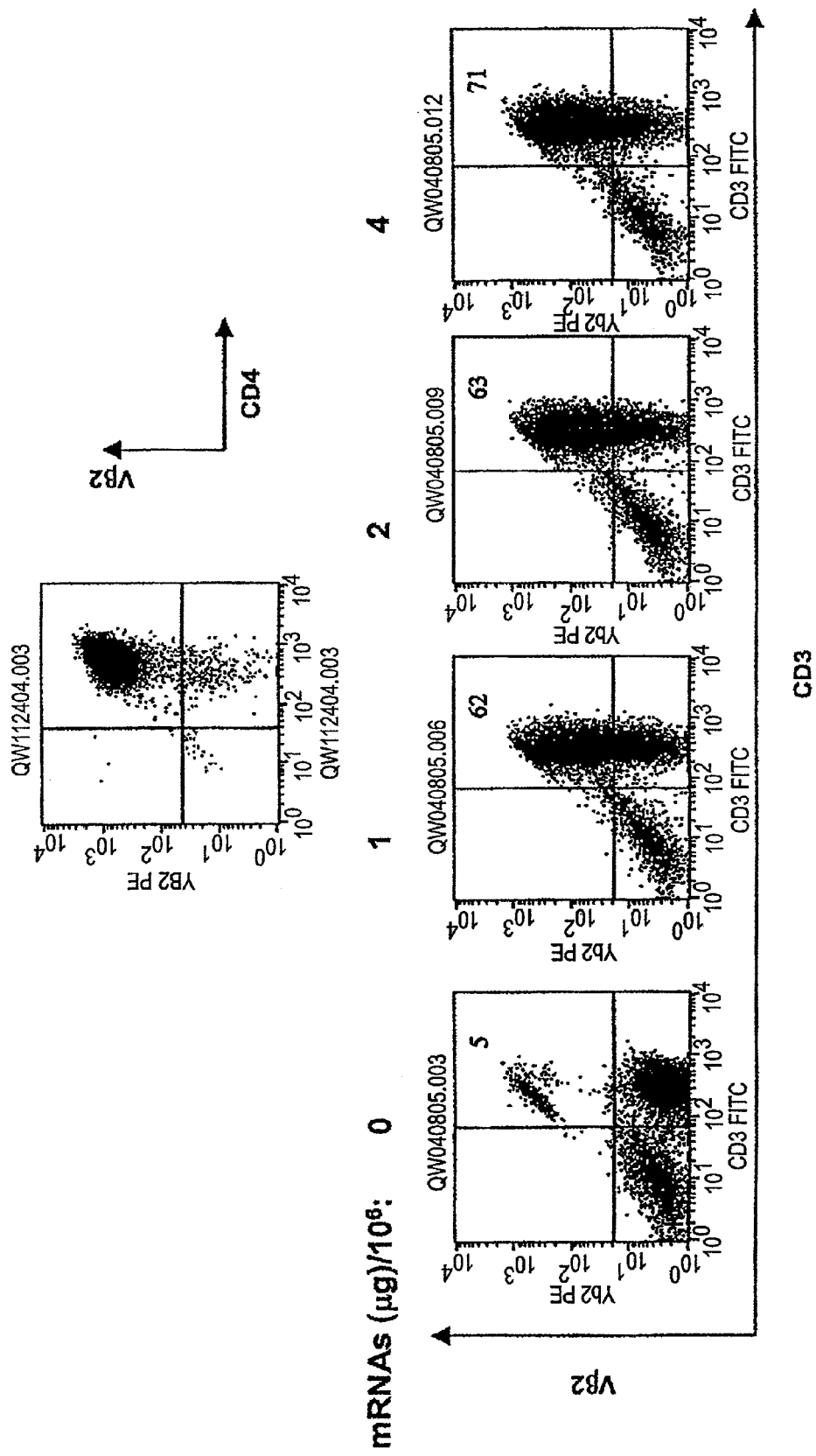

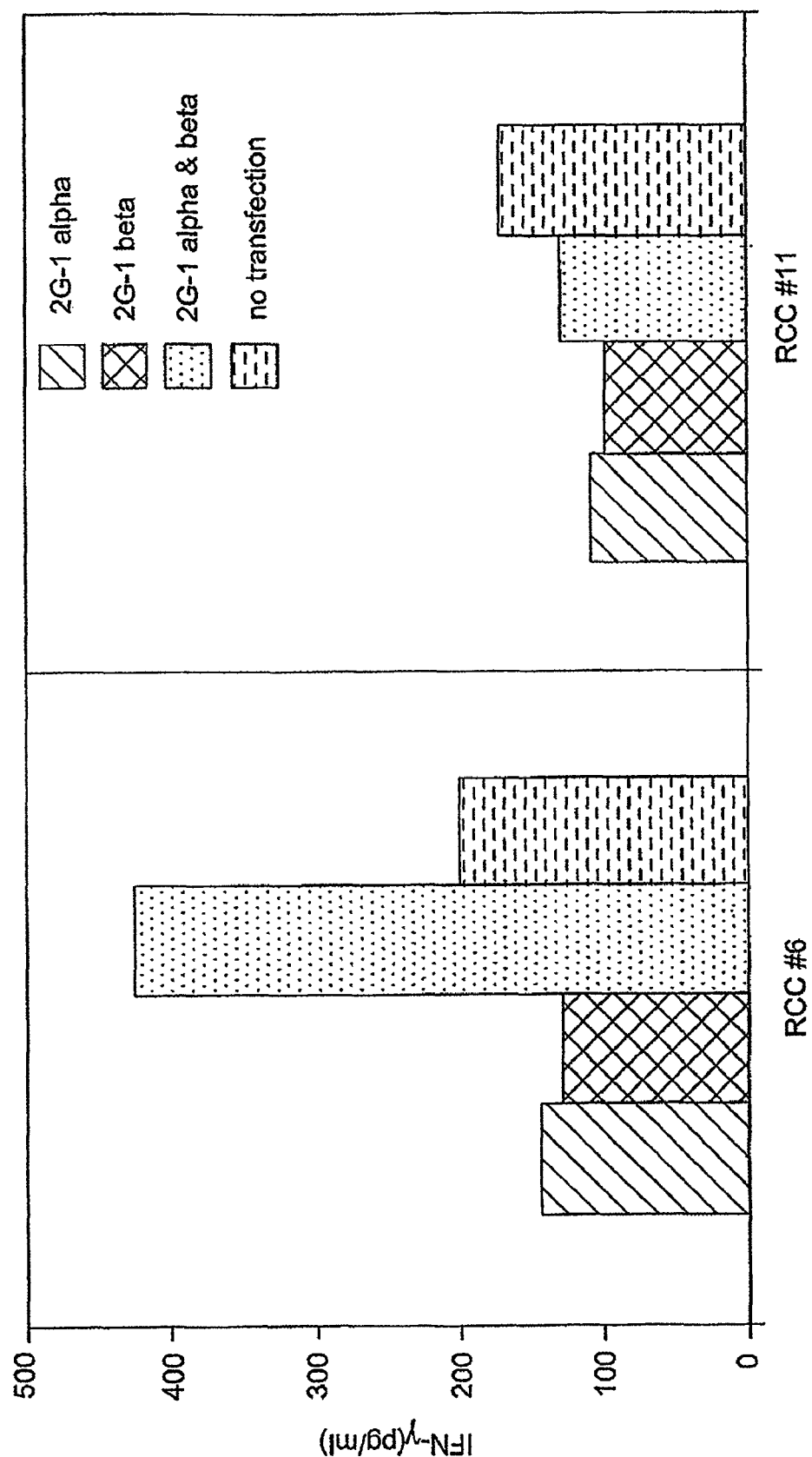

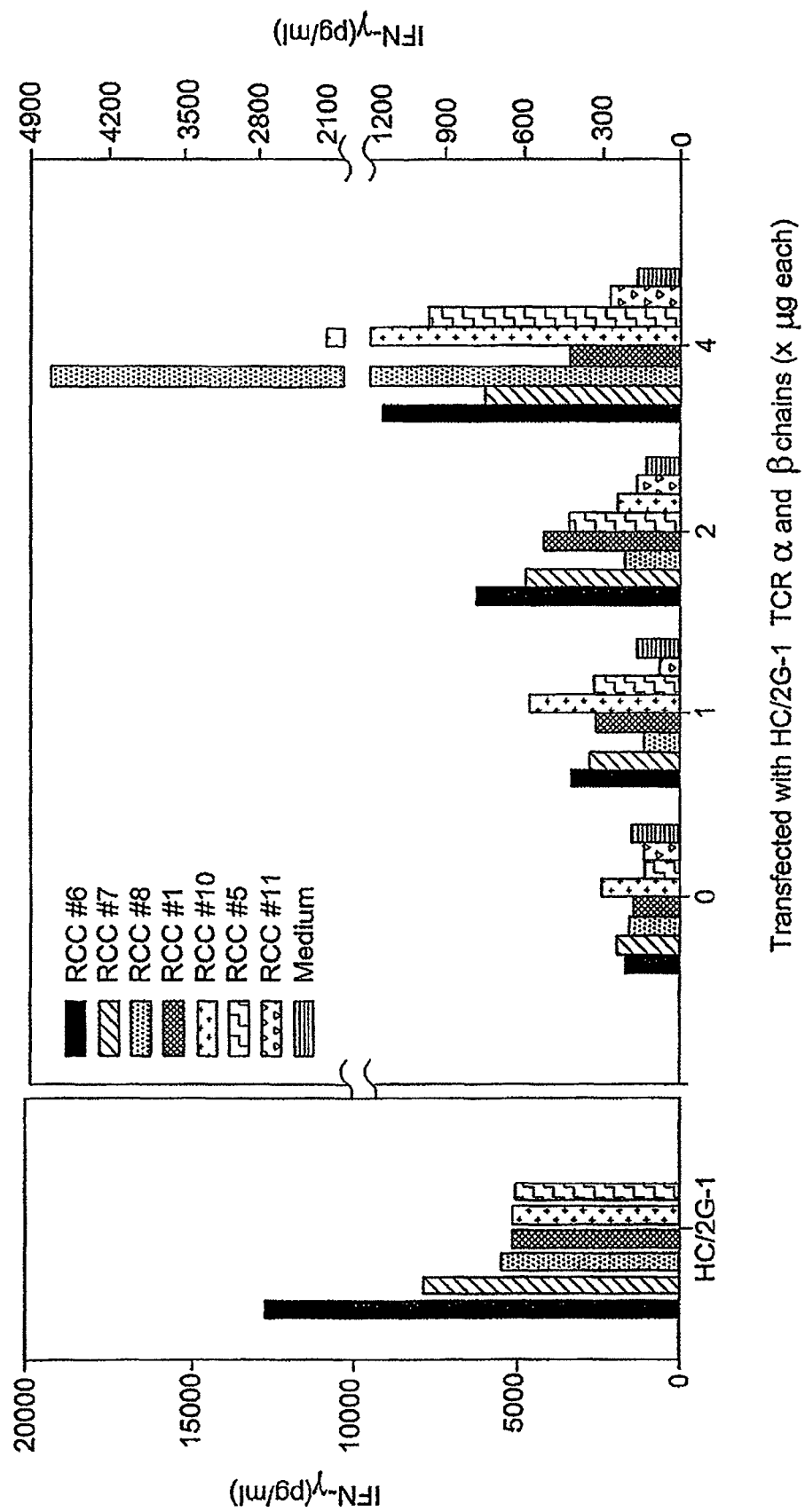

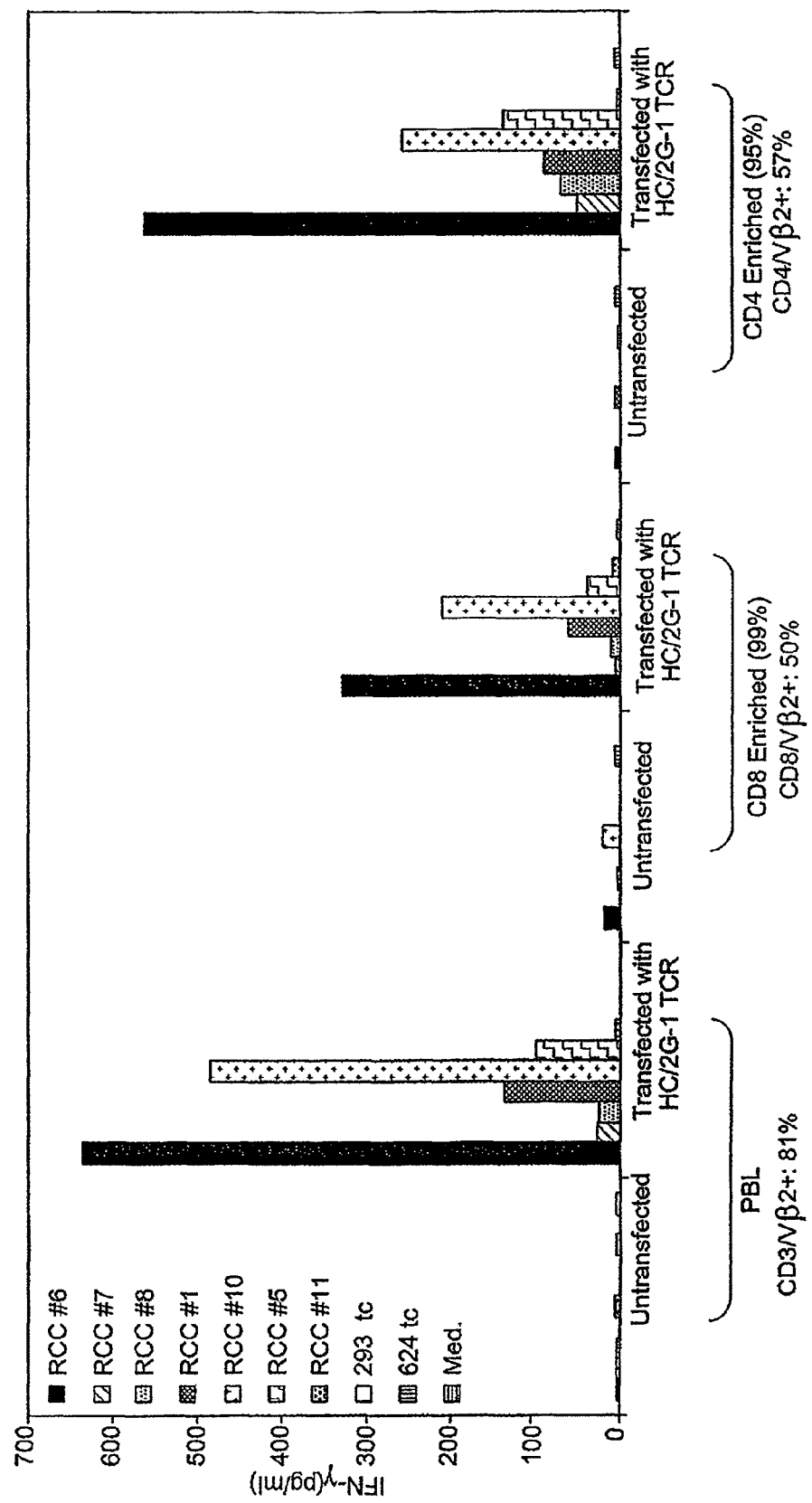

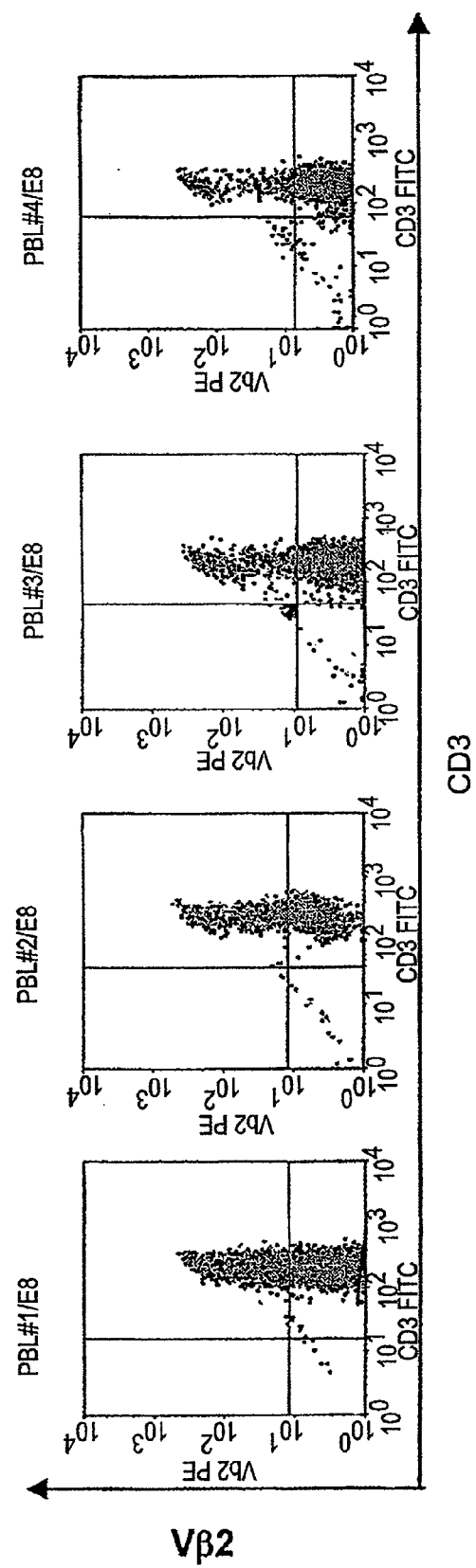

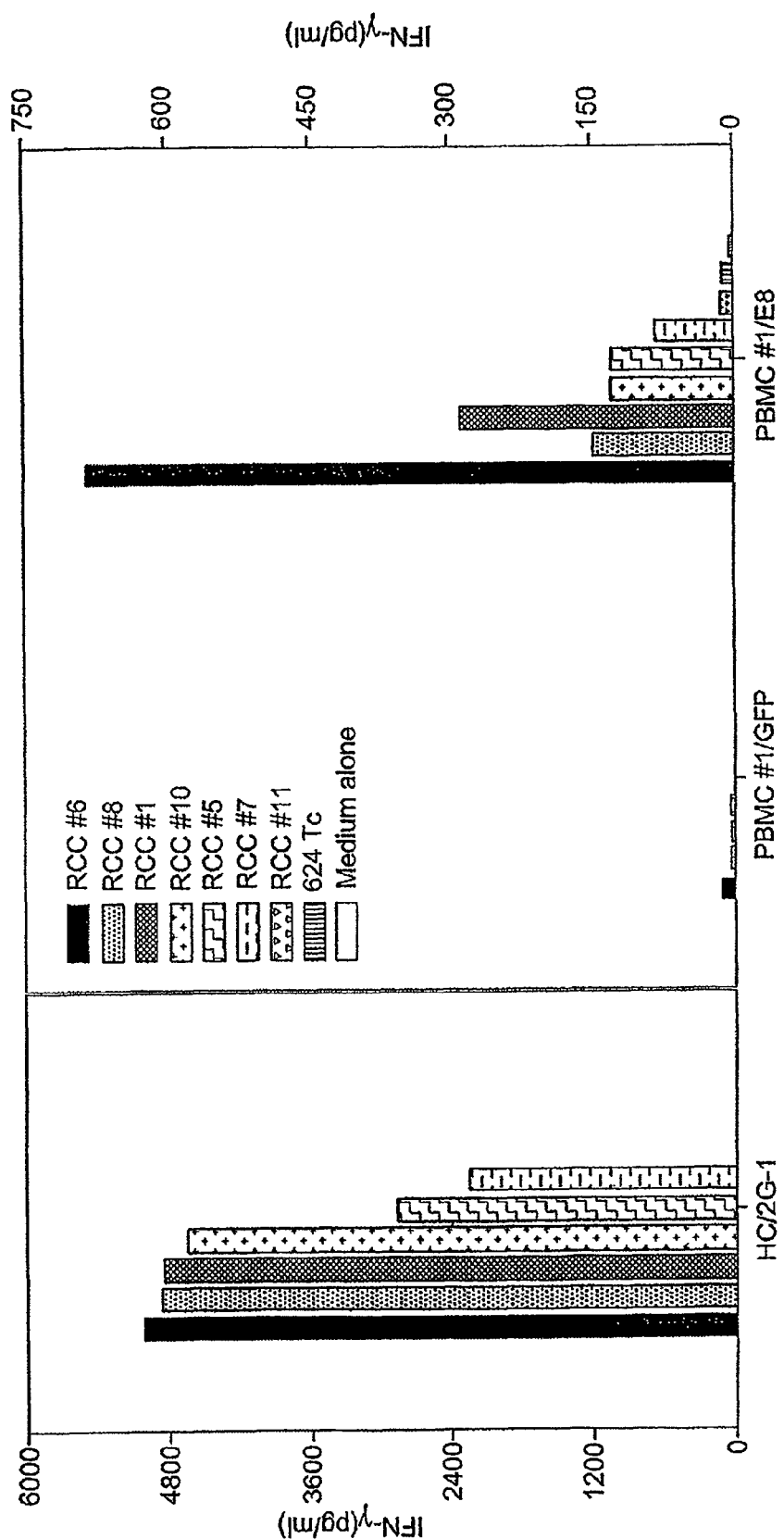

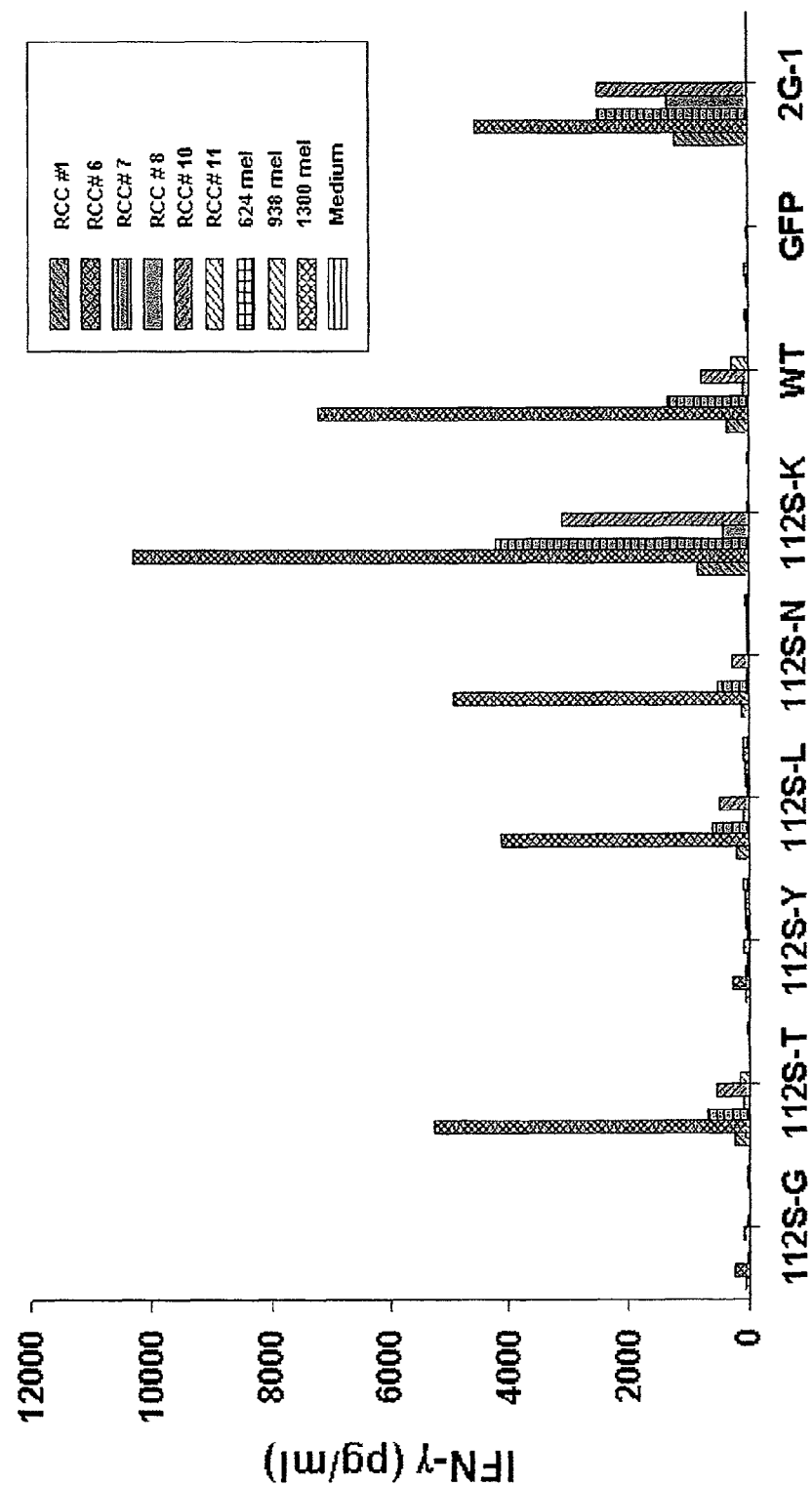

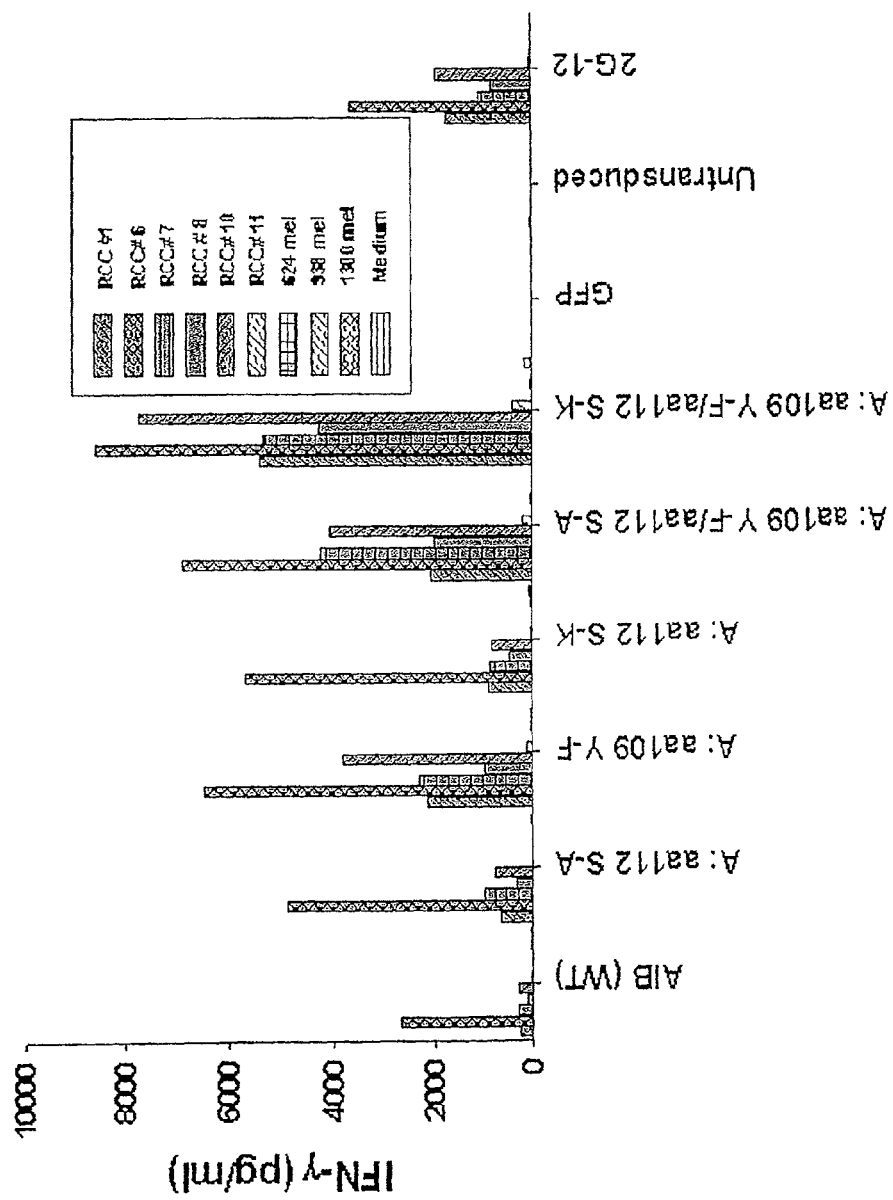

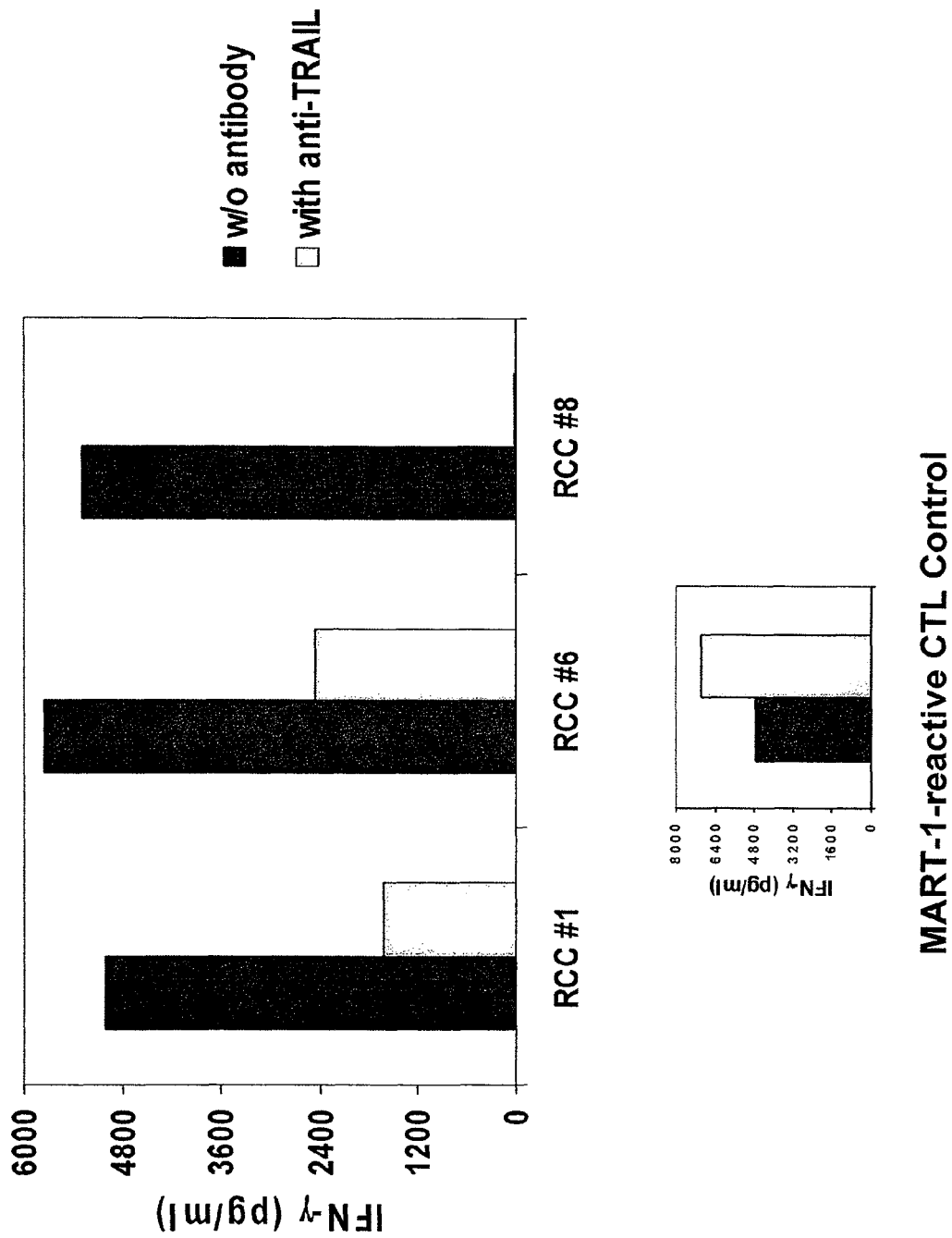

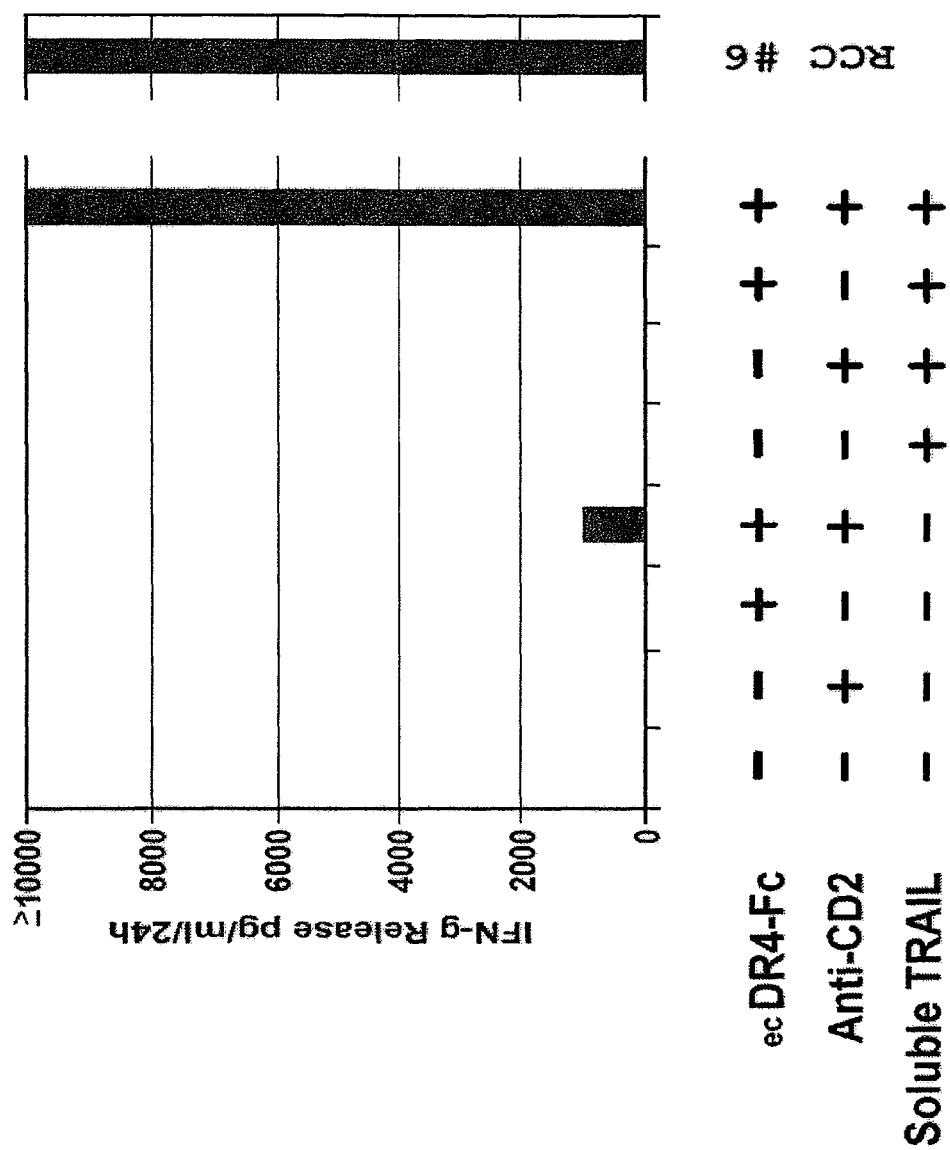

SEQUENCE LISTING

```
<160> NUMBER OF SEQ ID NOS: 36

<210> SEQ ID NO 1
<211> LENGTH: 953
<212> TYPE: DNA
<213> ORGANISM: Homo sapiens

<400> SEQUENCE: 1
aagcagtggt tcaacgcaga gtacgcgggg atttcttctc tcaccatgcc aggttcacct        60
cacagtacag agtcctgaaa ataaagaaga agatttttttt ttatctagaa aaggaaccaa       120
acatgtcact ttctagcctg ctgaaggtgg tcacagcttc actgtggcta ggacctggca       180
ttgcccagaa gataactcaa acccaaccag gaatgttcgt gcaggaaaag gaggccgtga       240
ctctggactg cacatatgac accagtgatc aaagttatgg tctcttctgg tacaagcagc       300
ccagcagtgg ggaaatgatt tttcttattt atcagggggtc ttatgacgag caaaatgcaa       360
cagaaggtcg ctactcattg aatttccaga aggcaagaaa atccgccaac cttgtcatct       420
ccgcttcaca actgggggac tcagcaatgt atttctgtgc aatgagagag tatccctcct       480
acgacaaggt gatatttggg ccagggacaa gcttatcagt cattccaaat atccagaacc       540
ctgaccctgc cgtgtaccag ctgagagact ctaaatccag tgacaagtct gtctgcctat       600
tcaccgattt tgattctcaa acaaatgtgt cacaaagtaa ggattctgat gtgtatatca       660
cagacaaaac tgtgctagac atgaggtcta tggacttcaa gagcaacagt gctgtggcct       720
ggagcaacaa atctgacttt gcatgtgcaa acgccttcaa caacagcatt attccagaag       780
acaccttctt ccccagccca gaaagttcct gtgatgtcaa gctggtcgag aaaagctttg       840
aaacagatac gaacctaaac tttcaaaacc tgtcagtgat tgggttccga atcctcctcc       900
tgaaagtggc cgggtttaat ctgctcatga cgctgcggct gtggtccagc tga             953

<210> SEQ ID NO 2
<211> LENGTH: 1007
<212> TYPE: DNA
<213> ORGANISM: Homo sapiens

<400> SEQUENCE: 2
aagcagtggt atcaacgcag agtacgcggg gggaggcagt ggccacaact ctccccagag        60
aaggtggtgt gaggccatca cggaagatgc tgctgcttct gctgcttctg gggccaggct       120
```

-continued

```
ccgggcttgg tgctgtcgtc tctcaacatc cgagctgggt tatctgtaag agtggaacct    180
ctgtgaagat cgagtgccgt tccctggact ttcaggccac aactatgttt tggtatcgcc    240
agttcccgaa acagagtctc atgctgatgg caacttccaa tgagggctcc aaggccacat    300
acgagcaagg cgtcgagaag acaagtttc tcatcaacca tgcaagcctg accttgtcca     360
ctctgacagt gaccagtgcc atcctgaaga cagcagctt ctacatctgc agtgctgata     420
ggggagtaaa cactgaagct ttctttggac aaggcaccag actcacagtt gtagaggacc    480
tgaacaaggt gttcccaccc gaggtcgctg tgtttgagcc atcagaagca gagatctccc    540
acacccaaaa ggccacactg gtgtgcctgg ccacaggctt cttccctgac acgtgggagc    600
tgagctggtg ggtgaatggg aaggaggtgc acagtgggt cagcacggac ccgcagcccc     660
tcaaggagca gcccgccctc aatgactcca gatactgcct gagcagccgc ctgagggtct    720
cggccacctt ctggcagaac ccccgcaacc acttccgctg tcaagtccag ttctacgggc    780
tctcggagaa tgacgagtgg acccaggata gggccaaacc cgtcacccag atcgtcagcg    840
ccgaggcctg gggtagagca gactgtggct ttacctcggt gtcctaccag caagggtcc     900
tgtctgccac catcctctat gagatcctgc tagggaaggc caccctgtat gctgtgctgg    960
tcagcgccct tgtgttgatg gccatggtca agagaaagga tttctga                 1007
```

```
<210> SEQ ID NO 3
<211> LENGTH: 276
<212> TYPE: PRT
<213> ORGANISM: Homo sapiens

<400> SEQUENCE: 3

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Tyr Pro Ser Tyr Asp Lys Val Ile Phe Gly Pro Gly
        115                 120                 125

Thr Ser Leu Ser Val Ile Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
```

```
                210                 215                 220
Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
                260                 265                 270

Leu Trp Ser Ser
275

<210> SEQ ID NO 4
<211> LENGTH: 306
<212> TYPE: PRT
<213> ORGANISM: Homo sapiens

<400> SEQUENCE: 4

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Asp Arg
            100                 105                 110

Gly Val Asn Thr Glu Ala Phe Phe Gly Gln Gly Thr Arg Leu Thr Val
        115                 120                 125

Val Glu Asp Leu Asn Lys Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
290                 295                 300
```

Asp Phe
305

<210> SEQ ID NO 5
<211> LENGTH: 348
<212> TYPE: DNA
<213> ORGANISM: Homo sapiens

<400> SEQUENCE: 5
atgtcacttt ctagcctgct gaaggtggtc acagcttcac tgtggctagg acctggcatt       60
gcccagaaga taactcaaac ccaaccagga atgttcgtgc aggaaaagga ggccgtgact      120
ctggactgca catatgacac cagtgatcaa agttatggtc tcttctggta caagcagccc      180
agcagtgggg aaatgatttt tcttatttat caggggtctt atgacgagca aaatgcaaca      240
gaaggtcgct actcattgaa tttccagaag gcaagaaaat ccgccaacct tgtcatctcc      300
gcttcacaac tgggggactc agcaatgtat ttctgtgcaa tgagagag                   348

<210> SEQ ID NO 6
<211> LENGTH: 330
<212> TYPE: DNA
<213> ORGANISM: Homo sapiens

<400> SEQUENCE: 6
atgctgctgc ttctgctgct tctggggcca ggctccgggc ttggtgctgt cgtctctcaa       60
catccgagct gggttatctg taagagtgga acctctgtga agatcgagtg ccgttccctg      120
gactttcagg ccacaactat gttttggtat cgccagttcc cgaaacagag tctcatgctg      180
atggcaactt ccaatgaggg ctccaaggcc acatacgagc aaggcgtcga aggacaag       240 tttctcatca accatgcaag cctgaccttg tccactctga cagtgaccag tgcccatcct      300
gaagacagca gcttctacat ctgcagtgct                                      330

<210> SEQ ID NO 7
<211> LENGTH: 116
<212> TYPE: PRT
<213> ORGANISM: Homo sapiens
<220> FEATURE:
<221> NAME/KEY: MISC_FEATURE
<223> OTHER INFORMATION: Amino acid sequence of TRAV14/DV4*02 for
      Valpha 14.

<400> SEQUENCE: 7

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu
        115

```
<210> SEQ ID NO 8
<211> LENGTH: 110
<212> TYPE: PRT
<213> ORGANISM: Homo sapiens
<220> FEATURE:
<221> NAME/KEY: MISC_FEATURE
<223> OTHER INFORMATION: Amino acid sequence of TRBV20-1 for Vbeta 2.

<400> SEQUENCE: 8

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala
            100                 105                 110

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
tcagctggac cacagccgca gc                                          22

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
tcagaaatcc tttctcttga ccatg                                       25

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
ctagcctctg gaatcctttc tcttg                                       25

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
tctagccatg gcactttcta gcctgc                                      26
```

```
<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
atagcggccg ctcagctgga ccacag                                             26

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
atctactcga gatgctgctg cttctgctgc tgcttctg                                38

<210> SEQ ID NO 15
<211> LENGTH: 35
<212> TYPE: DNA
<213> ORGANISM: Artificial Sequence
<220> FEATURE:
<223> OTHER INFORMATION: Synthetic

<400> SEQUENCE: 15
tctgcagaat tcggcttcag aaatcctttc tcttg                                   35

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Thr Ser Asp Gln Ser Tyr Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gln Gly Ser Tyr Asp Glu Gln
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Ala Met Arg Glu Tyr Pro Ser Tyr Asp Lys Val Ile
1               5                   10

<210> SEQ ID NO 19
<211> LENGTH: 6
```

```
<212> TYPE: PRT
<213> ORGANISM: Artificial Sequence
<220> FEATURE:
<223> OTHER INFORMATION: Synthetic

<400> SEQUENCE: 19

Asp Phe Gln Ala Thr Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Ser Asn Glu Gly Ser Lys Ala
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Ser Ala Asp Arg Gly Val Asn Thr Glu Ala Phe
1               5                   10

<210> SEQ ID NO 22
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (119)..(119)
<223> OTHER INFORMATION: Position 119 is selected from the group
      consisting of Lys and Ala.

<400> SEQUENCE: 22

Met Ala Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Tyr Pro Xaa Tyr Asp Lys Val Ile Phe Gly Pro Gly
        115                 120                 125

Thr Ser Leu Ser Val Ile Pro Asn Ile Gln Asn Pro Asp Pro Ala Val
    130                 135                 140

Tyr Gln Leu Arg Asp Ser Lys Ser Ser Asp Lys Ser Val Cys Leu Phe
```

```
                    145                 150                 155                 160
Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 23
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (117)..(117)
<223> OTHER INFORMATION: Position 117 is Phe.
<220> FEATURE:
<221> NAME/KEY: misc_feature
<222> LOCATION: (119)..(119)
<223> OTHER INFORMATION: Position 119 is selected from the group
      consisting of Lys, Ala, and Ser.

<400> SEQUENCE: 23

Met Ala Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Xaa Pro Xaa Tyr Asp Lys Val Ile Phe Gly Pro Gly
        115                 120                 125

Thr Ser Leu Ser Val Ile Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
```

```
                    180                 185                 190
Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 24
<211> LENGTH: 831
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (355)..(357)
<223> OTHER INFORMATION: nnn is aaa, aag, gca, gcc, gcg, or gct.

<400> SEQUENCE: 24
atggcacttt ctagcctgct gaaggtggtc acagcttcac tgtggctagg acctggcatt      60
gcccagaaga taactcaaac ccaaccagga atgttcgtgc aggaaaagga ggccgtgact     120
ctggactgca catatgacac cagtgatcaa agttatggtc tcttctggta caagcagccc     180
agcagtgggg aaatgatttt tcttatttat cagggtctt atgacgagca aaatgcaaca      240
gaaggtcgct actcattgaa tttccagaag gcaagaaaat ccgccaacct tgtcatctcc     300
gcttcacaac tgggggactc agcaatgtat ttctgtgcaa tgagagagta cccnnntac      360 gacaaggtga tatttgggcc agggacaagc ttatcagtca ttccaaatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca acagcattat tccagaagac     660
accttcttcc ccagcccaga aagttcctgt gatgtcaagc tggtcgagaa aagctttgaa     720
acagatacga acctaaactt tcaaaacctg tcagtgattg ggttccgaat cctcctcctg     780
aaagtggccg gtttaatct gctcatgacg ctgcggctgt ggtccagctg a               831

<210> SEQ ID NO 25
<211> LENGTH: 831
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (349)..(351)
<223> OTHER INFORMATION: nnn is ttc, or ttt.
<220> FEATURE:
<221> NAME/KEY: misc_feature
<222> LOCATION: (355)..(357)
<223> OTHER INFORMATION: nnn is aaa, aag, gca, gcc, gcg, gct, agc, agt,
      tca, tcc, tcg, or tct.
```

<400> SEQUENCE: 25

```
atggcacttt ctagcctgct gaaggtggtc acagcttcac tgtggctagg acctggcatt      60
gcccagaaga taactcaaac ccaaccagga atgttcgtgc aggaaaagga ggccgtgact     120
ctggactgca catatgacac cagtgatcaa agttatggtc tcttctggta caagcagccc     180
agcagtgggg aaatgatttt tcttatttat caggggtctt atgacgagca aaatgcaaca     240
gaaggtcgct actcattgaa tttccagaag gcaagaaaat ccgccaacct tgtcatctcc     300
gcttcacaac tgggggactc agcaatgtat ttctgtgcaa tgagagagnn ncccnnntac     360
gacaaggtga tatttgggcc agggacaagc ttatcagtca ttccaaatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca acagcattat tccagaagac     660
accttcttcc ccagcccaga aagttcctgt gatgtcaagc tggtcgagaa aagctttgaa     720
acagatacga acctaaactt tcaaaacctg tcagtgattg gttccgaat cctcctcctg      780
aaagtggccg ggtttaatct gctcatgacg ctgcggctgt ggtccagctg a              831
```

<210> SEQ ID NO 26
<211> LENGTH: 125
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (119)..(119)
<223> OTHER INFORMATION: "Xaa" is selected from the group consisting of Lys and Ala.

<400> SEQUENCE: 26

```
Met Ala Leu Ser Ser Leu Leu Lys Val Val Thr Ala Ser Leu Trp Leu
1               5                   10                  15
Gly Pro Gly Ile Ala Gln Lys Ile Thr Gln Thr Gln Pro Gly Met Phe
            20                  25                  30
Val Gln Glu Lys Glu Ala Val Thr Leu Asp Cys Thr Tyr Asp Thr Ser
        35                  40                  45
Asp Gln Ser Tyr Gly Leu Phe Trp Tyr Lys Gln Pro Ser Ser Gly Glu
    50                  55                  60
Met Ile Phe Leu Ile Tyr Gln Gly Ser Tyr Asp Glu Gln Asn Ala Thr
65                  70                  75                  80
Glu Gly Arg Tyr Ser Leu Asn Phe Gln Lys Ala Arg Lys Ser Ala Asn
                85                  90                  95
Leu Val Ile Ser Ala Ser Gln Leu Gly Asp Ser Ala Met Tyr Phe Cys
            100                 105                 110
Ala Met Arg Glu Tyr Pro Xaa Tyr Asp Lys Val Ile Phe
        115                 120                 125
```

<210> SEQ ID NO 27
<211> LENGTH: 125
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (117)..(117)

```
<223> OTHER INFORMATION: "Xaa" is Phe.
<220> FEATURE:
<221> NAME/KEY: misc_feature
<222> LOCATION: (119)..(119)
<223> OTHER INFORMATION: "Xaa" is selected from the group consisting of
      Lys, Ala, and Ser.

<400> SEQUENCE: 27

Met Ala Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Xaa Pro Xaa Tyr Asp Lys Val Ile Phe
        115                 120                 125

<210> SEQ ID NO 28
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: "Xaa" is selected from the group consisting of
      Lys and Ala.

<400> SEQUENCE: 28

Ala Met Arg Glu Tyr Pro Xaa Tyr Asp Lys Val Ile Phe
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: "Xaa" is Phe.
<220> FEATURE:
<221> NAME/KEY: misc_feature
<222> LOCATION: (7)..(7)
<223> OTHER INFORMATION: "Xaa" is selected from the group consisting of
      Lys, Ala, and Ser.

<400> SEQUENCE: 29

Ala Met Arg Glu Xaa Pro Xaa Tyr Asp Lys Val Ile Phe
1               5                   10

<210> SEQ ID NO 30
<211> LENGTH: 831
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (349)..(351)
<223> OTHER INFORMATION: nnn is ttc or ttt.
<220> FEATURE:
<221> NAME/KEY: misc_feature
<222> LOCATION: (355)..(357)
<223> OTHER INFORMATION: nnn is aaa or aag

<400> SEQUENCE: 30
atggccctga gcagcctgct gaaggtggtg accgccagcc tgtggctggg acccggcatt      60
gcccagaaga tcacccagac ccagcccggc atgttcgtgc aggaaaaaga agccgtcacc     120
ctggactgca cctacgacac cagcgaccag agctacggcc tgttctggta caagcagccc     180
agcagcggcg agatgatctt cctgatctac cagggcagct acgacgagca gaacgccacc     240
gagggccggt acagcctgaa cttccagaag gcccggaaga gcgccaacct ggtgatcagc     300
gccagccagc tgggcgacag cgccatgtac ttttgcgcca tgagagagnn nccnnntac     360 gacaaggtga tcttcggccc tggcaccagc ctgagcgtga tccccaacat ccagaacccc     420
gaccccgccg tgtaccagct gcgggacagc aagagcagcg acaagagcgt gtgcctgttc     480
accgacttcg acagccagac caacgtgagc cagagcaagg acagcgacgt gtacatcacc     540
gacaagaccg tgctggacat gcggagcatg gacttcaaga gcaacagcgc cgtggcctgg     600
tccaacaaga gcgacttcgc ctgcgccaac gccttcaaca acagcatcat ccccgaggac     660 accttttttcc ccagccccga gagcagctgc gacgtgaaac tggtggagaa gagcttcgag     720
acagacacca acctgaattt tcagaacctg tccgtgatcg gcttccggat cctgctgctg     780
aaagtggccg gcttcaacct gctcatgacg ctgcggctgt ggtccagctg a     831

<210> SEQ ID NO 31
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (349)..(351)
<223> OTHER INFORMATION: nnn is ttc or ttt.
<220> FEATURE:
<221> NAME/KEY: misc_feature
<222> LOCATION: (355)..(357)
<223> OTHER INFORMATION: nnn is aaa or aag.

<400> SEQUENCE: 31
atggccctga gcagcctgct gaaggtggtg accgccagcc tgtggctggg acccggcatt      60
gcccagaaga tcacccagac ccagcccggc atgttcgtgc aggaaaaaga agccgtcacc     120
ctggactgca cctacgacac cagcgaccag agctacggcc tgttctggta caagcagccc     180
agcagcggcg agatgatctt cctgatctac cagggcagct acgacgagca gaacgccacc     240
gagggccggt acagcctgaa cttccagaag gcccggaaga gcgccaacct ggtgatcagc     300
gccagccagc tgggcgacag cgccatgtac ttttgcgcca tgagagagnn nccnnntac     360 gacaaggtga tcttc                                                       375

<210> SEQ ID NO 32
<211> LENGTH: 39
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (13)..(15)
<223> OTHER INFORMATION: nnn is ttc or ttt.
<220> FEATURE:
<221> NAME/KEY: misc_feature
<222> LOCATION: (19)..(21)
<223> OTHER INFORMATION: nnn is aaa or aag.

<400> SEQUENCE: 32
gccatgagag agnnncccnn ntacgacaag gtgatcttc                              39

<210> SEQ ID NO 33
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (355)..(357)
<223> OTHER INFORMATION: nnn is aaa, aag, gca, gcc, gcg, or gct.

<400> SEQUENCE: 33
atggcacttt ctagcctgct gaaggtggtc acagcttcac tgtggctagg acctggcatt       60
gcccagaaga taactcaaac ccaaccagga atgttcgtgc aggaaaagga ggccgtgact      120
ctggactgca catatgacac cagtgatcaa agttatggtc tcttctggta caagcagccc      180
agcagtgggg aaatgatttt tcttatttat caggggtctt atgacgagca aaatgcaaca      240
gaaggtcgct actcattgaa tttccagaag gcaagaaaat ccgccaacct tgtcatctcc      300
gcttcacaac tgggggactc agcaatgtat ttctgtgcaa tgagagagta ccccnnntac      360
gacaaggtga tattt                                                      375

<210> SEQ ID NO 34
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (349)..(351)
<223> OTHER INFORMATION: nnn is ttc or ttt.
<220> FEATURE:
<221> NAME/KEY: misc_feature
<222> LOCATION: (355)..(357)
<223> OTHER INFORMATION: nnn is aaa, aag, gca, gcc, gcg, gct, agc, agt,
      tca, tcc, tcg, or tct.

<400> SEQUENCE: 34
atggcacttt ctagcctgct gaaggtggtc acagcttcac tgtggctagg acctggcatt       60
gcccagaaga taactcaaac ccaaccagga atgttcgtgc aggaaaagga ggccgtgact      120
ctggactgca catatgacac cagtgatcaa agttatggtc tcttctggta caagcagccc      180
agcagtgggg aaatgatttt tcttatttat caggggtctt atgacgagca aaatgcaaca      240
gaaggtcgct actcattgaa tttccagaag gcaagaaaat ccgccaacct tgtcatctcc      300
gcttcacaac tgggggactc agcaatgtat ttctgtgcaa tgagagagnn ncccnnntac      360
gacaaggtga tattt                                                      375

<210> SEQ ID NO 35
<211> LENGTH: 39
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (19)..(21)
<223> OTHER INFORMATION: nnn is aaa, aag, gca, gcc, gcg, or gct.

<400> SEQUENCE: 35
gcaatgagag agtatcccnn ntacgacaag gtgatattt                              39

<210> SEQ ID NO 36
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(15)
<223> OTHER INFORMATION: nnn is ttc or ttt.
<220> FEATURE:
<221> NAME/KEY: misc_feature
<222> LOCATION: (19)..(21)
<223> OTHER INFORMATION: nnn is aaa, aag, gca, gcc, gcg, gct, agc, agt,
      tca, tcc, tcg, or tct.

<400> SEQUENCE: 36
gcaatgagag agnnncccnn ntacgacaag gtgatattt                              39
```

T CELL RECEPTORS AND RELATED MATERIALS AND METHODS OF USE

CROSS-REFERENCE TO RELATED APPLICATIONS

This patent application is a continuation-in-part of copending International Patent Application No. PCT/US07/04454, filed Feb. 22, 2007, which claims the benefit of U.S. Provisional Patent application No. 60/776,194, filed Feb. 24, 2006, and U.S. Provisional Patent Application No. 60/811,422, filed Jun. 7, 2006, which are each incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 21,883 Byte ASCII (Text) file named "703194ST25TXT," created on Aug. 15, 2008.

Applicants request entry into the specification of the Sequence listing submitted herewith.

BACKGROUND OF THE INVENTION

Clear cell renal cell carcinoma (RCC) is the most common renal tumor with an incidence of about 30,000 cases per year in the United States (Motzer et al., *New Engl. J. Med.* 335: 865-875 (1996)). For patients with metastatic RCC, the 5-year survival rate is approximately 10% because RCC is highly resistant to most chemotherapies (Motzer et al., *J. Urol.* 163: 408-417 (2000)). RCC has been considered immunogenic, and 10-20% of RCC patients with metastases can respond to cytokine-based therapy (e.g., interleukin (IL)-2 or IL-2 combined with interferon (IFN)-α) (Yang et al., *J. Clin. Oncol.* 21: 3127-3132 (2003); Tourani et al., *J. Clin. Oncol.* 21: 3987-3994 (2003)) with some of these patients appearing to be cured.

Despite the immunogenicity of RCC, there has been little progress in treating metastatic RCC patients with immunotherapy since the advent of IL-2 (Bleumer et al., *Eur. Urol.* 44: 65-75 (2003)). There have been major problems in defining the molecular basis of the immune response to RCC, in contrast to the rapid progress with human melanoma. This is largely due to a lack of a source of RCC-reactive T cells, again in contrast to melanoma, where IL-2 cultured tumor-infiltrating lymphocytes are often tumor reactive. Recently, Hanada et al. successfully generated a $CD8^+$ T-cell clone from a patient with metastatic RCC, which recognized fibroblast growth factor (FGF)-5 (Hanada et al., *Cancer Res.* 61: 5511-5516 (2001); Hanada et al., *Nature* 427: 252-256 (2004)). FGF-5 proved to be one of a few RCC antigens that are suitable for clinical therapy because it is overexpressed in many tumors, but not in normal tissues. Yet, this remains only one of very few successful examples of generating RCC-reactive T cells by culturing TILs.

In view of the foregoing, there is a need in the art for RCC-reactive T cells for use in treating RCC patients. The invention provides such T cells and methods of treating cancer, especially RCC.

BRIEF SUMMARY OF THE INVENTION

The invention provides an isolated or purified T cell receptor (TCR) having antigenic specificity for a cancer antigen, e.g., a renal cell carcinoma antigen, wherein the TCR recognizes the cancer antigen in a major histocompatibility complex (MHC)-independent manner. The TCR can comprise specified amino acid sequences as described herein. For instance, the inventive TCR can comprise the amino acid sequence of SEQ ID NOs: 16-21, SEQ ID NOs: 16-17, 28 and 19-21, SEQ ID NOs: 16-17, 29 and 19-21, SEQ ID NOs: 7 and 8, SEQ ID NOs: 26 and 8, SEQ ID NOs: 27 and 8, SEQ ID NOs: 3 and 4, SEQ ID NOs: 22 and 4, or SEQ ID NOs: 23 and 4.

The invention further provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention.

Methods of detecting the presence of cancer in a host and methods of treating or preventing cancer in a host are further provided by the invention. The inventive method of detecting the presence of cancer in a host comprises (i) contacting a sample comprising cells of the cancer with any of the inventive TCRs, polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of cancer in the host.

The inventive method of treating or preventing cancer in a host comprises administering to the host any of the TCRs, polypeptides, or proteins described herein, any nucleic acid or recombinant expression vector comprising a nucleotide sequence encoding any of the TCRs, polypeptides, proteins described herein, or any host cell or population of host cells comprising a recombinant vector which encodes any of the TCRs, polypeptides, or proteins described herein, in an amount effective to treat or prevent cancer in the host.

BRIEF DESCRIPTION OF THE SEVERAL VIEWS OF THE DRAWING(S)

FIG. 1A is a graph of the IFN-γ secretion (pg/ml) by cells of Microwell HC/2G upon stimulation with autologous EBV-B (EBV-B #1) or RCC (RCC #1) cells.

FIG. 1B is a graph of the IFN-γ secretion (pg/ml) by HC/2G-1 T cell clones upon stimulation with a panel of HLA-mismatched renal tumors (RCC #1-11), EBV-Bs (EBV-B #1-11 and 888 EBV-B), melanoma tumors (888 Tc, 624 Tc, 938 Tc, 526 Tc, 1937 Tc, 2370 Tc, 2195 Tc, 2359 Tc, and 2230 Tc), other tumor lines (BIC, BE-3, TC71, MDA435S, MDA386, SKN-AS, H2228, H2087, 293 Tc, COS7), normal epithelial and fibroblasts (MJW90, WLC89, MAS90, HRE1, HRE2, 1290 Fibr., 1383 Fibr., 1102 Fibr., 1700 Fibr., 1612 Fibr., and Fibr. #6).

FIG. 1C is a graph of the % specific lysis of target cells by HC/2G-1 T cell clones at the indicated effector cell:target cell (E:T) ratios. The target cells included RCC tumor cells (RCC #1 (dotted line with ♦), RCC #2 (dashed line with ●), RCC # 5 (solid line with ▼), RCC #6 (dotted line with ■), RCC #7 (dashed line with ♦), RCC #8 (dashed and dotted line with ▲), RCC #9 (dashed line with ●), and RCC #10 (dashed and dotted line with ●)) and negative controls (RCC #11 (dashed line with V), EBV-B #1 (solid line with ■), ELW91 (solid line with ●), MAS90 (dotted line with ▼), MJW90 (dashed line with ■), WLC89 (dashed line with ♦), K562 (dashed line with ▲), and Daudi (dashed and dotted line with ●) cells).

FIG. 2A is a set of flow cytometry graphs of HC/2G-1 cells stained with PE-labeled mouse $IgG_1$ antibody and FITC-labeled mouse IgG₁ antibody (first graph on left), PE-labeled anti-CD3 antibody and FITC-labeled anti-CD4 antibody (second graph from left), PE-labeled anti-CD56 antibody and FITC-labeled anti-CD16 antibody (third graph from left), PE-labeled anti-CD161 antibody and FITC-labeled anti-CD57 antibody (fourth graph from left), and PE-labeled anti-CD3 antibody and FITC-labeled anti-TCR γ/δ (g/d) chains antibody (fifth graph from left).

FIG. 3A is a flow cytometry graph of HC/2G-1 cells stained with PE-labeled TCR α/β chain antibody (solid line) and with an isotype-matched control antibody (PE-labeled anti-IgG₁; dotted line).

FIG. 3B is a set of graphs of the IFN-γ secretion (pg/ml) by HC/2G-1 T cell clones (top graph), MW 5H-5 cells (middle graph), and HC 10C-3 cells (bottom graph) upon stimulation with autologous RCC cells pre-treated without (No Ab) or with anti-HLA Class I, anti-HLA Class II, anti-TCR α/β (TCR a/b), or anti-CD4 antibodies.

FIG. 4A is a set of flow cytometry graphs of HC/2G-1 cells stained with PE-labeled Vβ2 antibody and FITC-labeled anti-CD4 antibody (top) and of cells electroporated with mRNA encoding the TCR of HC/2G-1 cells (bottom row) with 0 (first graph on left), 1 (second graph from the left), 2 (third graph from left), and 4 (fourth graph from the left) μg per 10⁶ cells stained with PE-labeled Vβ2 antibody and FITC-labeled anti-CD3 antibody.

FIG. 4B is a graph of the IFN-γ secretion (pg/ml) by cells electroporated with mRNA encoding the α chain of the HC/2G-1 TCR (vertical lined bars), the β chain of the HC/2G-1 TCR (crisscrossed bars), or both chains of the HC/2G-1 TCR (dotted bars), or untransfected (dashed lined bars) upon stimulation with RCC #6 cells (left panel) or negative control cells (RCC #11 cells; right panel).

FIG. 4C is a graph of the IFN-γ secretion (pg/ml) by cells electroporated with 0, 1, 2, or 4 μg mRNA encoding both chains of the HC/2G-1 TCR upon stimulation with RCC cells (RCC #1 (crisscrossed bars), RCC #5 (zigzagged bars), RCC #6 (solid bars), RCC #7 (diagonal lined bars), RCC #8 (dotted bars), RCC #10 (bars with plus signs bars), and RCC #11 (bars with triangles)) or with medium only (horizontal lined bars). Also shown (left panel) is the IFN-γ secretion (pg/ml) by positive control cells (HC/2G-1 cells).

FIG. 4D is a graph of the IFN-γ secretion (pg/ml) by PBLs transfected with mRNA encoding HC/2G-1 TCR or untransfected and non-enriched (PBL) or enriched for CD8 (CD8 enriched) or CD4 (CD4 enriched) expression upon stimulation with RCC tumor cells (RCC #1 (crisscrossed bars), RCC #5 (zigzagged bars), RCC #6 (solid bars), RCC #7 (diagonal lined bars), RCC #8 (dotted bars), RCC #10 (bars with plus signs), and RCC #11 (bars with triangles)), with human embryonic kidney cells transduced with adenovirus (293 Tc (open bars)), with melanoma cells (624 Tc (vertical lined bars)), or with medium only (horizontal lined bars).

Figure 5A:
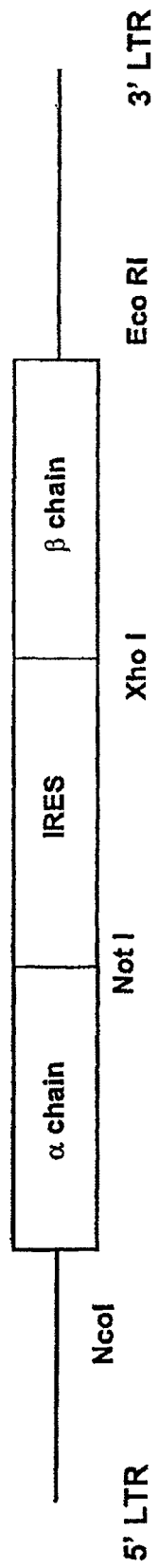

FIG. 5A is an illustration of the retroviral vector encoding the HC/2G-1 TCR used to transduce cells.

FIG. 5B is a set of flow cytometry graphs of PBMCs from allogeneic donors (#1-4; first, second, third, and fourth graphs from the left, respectively) transduced with retroviral vector encoding HC/2G-1 TCR and stained with PE-labeled anti-Vβ2 antibody (y-axis) or FITC-labeled anti-CD3 antibody (x-axis).

FIG. 5C is a graph of the IFN-γ secretion (pg/ml) by PBMCs from allogeneic donor #1 transduced with retroviral vector encoding GFP (PBMC #1/GFP) or HC/2G-1 TCR (PBMC #1/E8) upon stimulation with RCC tumor cells (RCC #1 (crisscrossed bars), RCC #5 (zigzagged bars), RCC #6 (solid bars), RCC #7 (dashed lined bars), RCC #8 (dotted bars), RCC #10 (bars with plus signs), and RCC #11 (bars with triangles)), with melanoma tumor cells (624 Tc; vertical lined bars), or with medium alone (open bars).

Figure 5D:
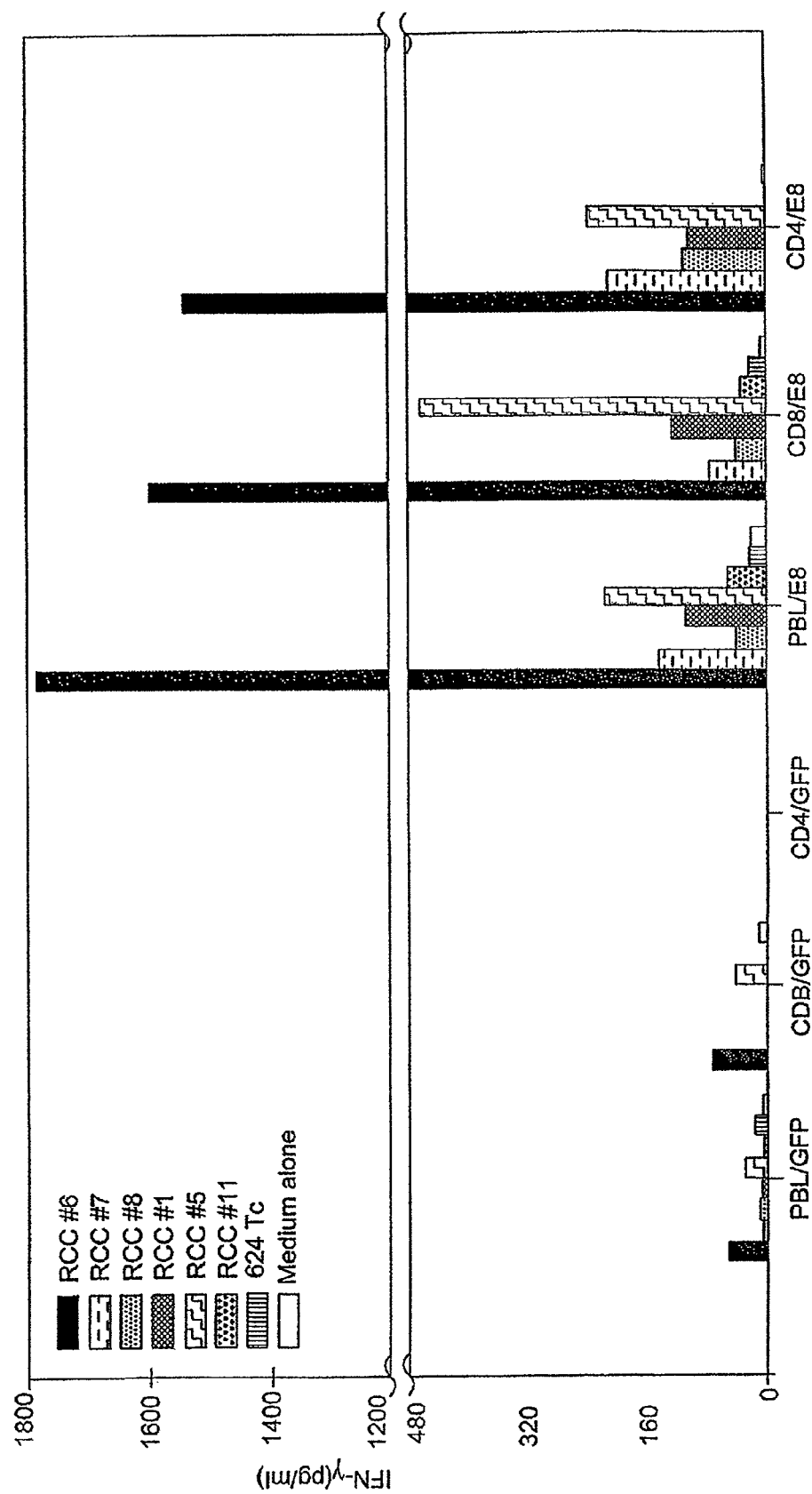

FIG. 5D is a graph of the IFN-γ secretion (pg/ml) by PBMCs transduced with retroviral vector encoding GFP (PBL/GFP) or HC/2G-1 TCR (PBL/E8) and enriched for CD8 (CD8/GFP and CD8/E8) or CD4 (CD4/GFP and CD4/E8) expression upon stimulation with RCC tumor cells (RCC #1 (crisscrossed bars), RCC #5 (zigzagged bars), RCC #6 (solid bars), RCC #7 (dashed lined bars), RCC #8 (dotted bars), and RCC #11 (bars with triangles)) or with melanoma tumor cells (624 Tc cells (vertical lined bars), or with medium alone (open bars).

Figure 6A:
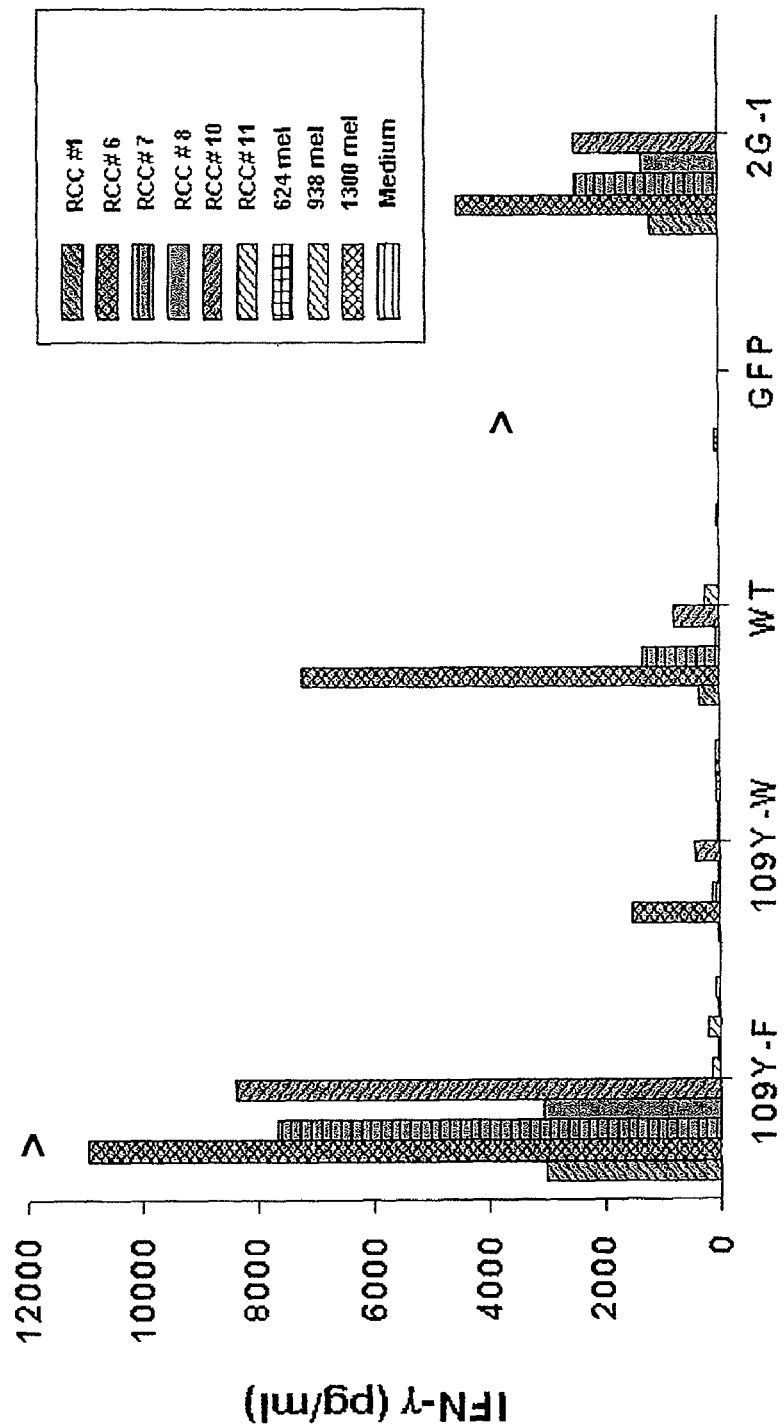

FIG. 6A is a graph of the IFN-γ secretion (pg/ml) by HC/2G-1 T cell clones (HC/2G-1), PBLs transduced with retroviral vector encoding GFP (GFP), unsubstituted TCR (WT), TCR including SEQ ID NO:23, wherein Xaa117 is Trp and Xaa119 is Ser (109Y-W), TCR including SEQ ID NO:23, wherein Xaa117 is Phe and Xaa119 is Ser (109 Y-F), and stimulated with RCC tumor cells (RCC #1 (gray forward slant bars), RCC #6 (gray crisscrossed bars), RCC #7 (gray horizontal line bars), RCC #8 (empty gray bars), RCC #10 (gray backward slant bars), and RCC #11 (white forward slant bars)) or with melanoma tumor cells (624mel cells (white squared bars), 938mel cells (white forward slant bars), 1300mel cells (white crisscrossed bars) or cultured in medium alone (white horizontal line bars)).

FIG. 6B is a graph of the IFN-γ secretion (pg/ml) by HC/2G-1 T cell clones (HC/2G-1), PBLs transduced with retroviral vector encoding GFP (GFP), unsubstituted TCR (WT), TCR including SEQ ID NO:22, wherein Xaa119 is Lys (112S-K), TCR including SEQ ID NO:22, wherein Xaa119 is Asn (112S-N), TCR including SEQ ID NO:22, wherein Xaa119 is Leu (112S-L), TCR including SEQ ID NO:22, wherein Xaa119 is Tyr (112S-Y), TCR including SEQ ID NO:22, wherein Xaa119 is Thr (112S-T), TCR including SEQ ID NO:22, wherein Xaa119 is Gly (112S-G) and stimulated with RCC tumor cells (RCC #1 (gray forward slant bars), RCC #6 (gray crisscrossed bars), RCC #7 (gray horizontal line bars), RCC #8 (empty gray bars), RCC #10 (gray backward slant bars), and RCC #11 (white forward slant bars)) or with melanoma tumor cells (624mel cells (white squared bars), 938mel cells (white forward slant bars), 1300mel cells (white crisscrossed bars) or cultured in medium alone (white horizontal line bars)).

FIG. 6C is a graph of the IFN-γ secretion (pg/ml) by HC/2G-1 T cell clones (2G-12), untransduced PBLs and PBLs transduced with retroviral vector encoding GFP (GFP), unsubstituted TCR (AIB(WT)), TCR including SEQ ID NO:22, wherein Xaa119 is Ala (A:aa112 S-A), TCR including SEQ ID NO:23, wherein Xaa117 is Phe and Xaa119 is Ser (A:aa109 Y-F), TCR including SEQ ID NO:22, wherein Xaa119 is Lys (A:aa112 S-K), TCR including SEQ ID NO:23, wherein Xaa117 is Phe and Xaa119 is Ala (A:aa109 Y-F/aa112 S-A), TCR including SEQ ID NO:23, wherein Xaa117 is Phe and Xaa119 is Lys (A:aa109 Y-F/aa112 S-K), and stimulated with RCC tumor cells (RCC #1 (gray forward slant bars), RCC #6 (gray crisscrossed bars), RCC #7 (gray horizontal line bars), RCC #8 (empty gray bars), RCC #10 (gray backward slant bars), and RCC #11 (white forward slant bars)) or with melanoma tumor cells (624mel cells (white squared bars), 938mel cells (white forward slant bars), 1300mel cells (white crisscrossed bars) or cultured in medium alone (white horizontal line bars)).

FIG. 7 is a graph of the IFN-γ secretion (pg/ml) by HC/2G-1 T-cell clones upon stimulation with RCC #1 cells, RCC #6 cells, RCC #8 cells (top panel) or MART-1-reactive CTL control cells (bottom panel) in the presence of anti-TRAIL antibody (right bars) or in the absence of antibody (left bars).

Figure 8:
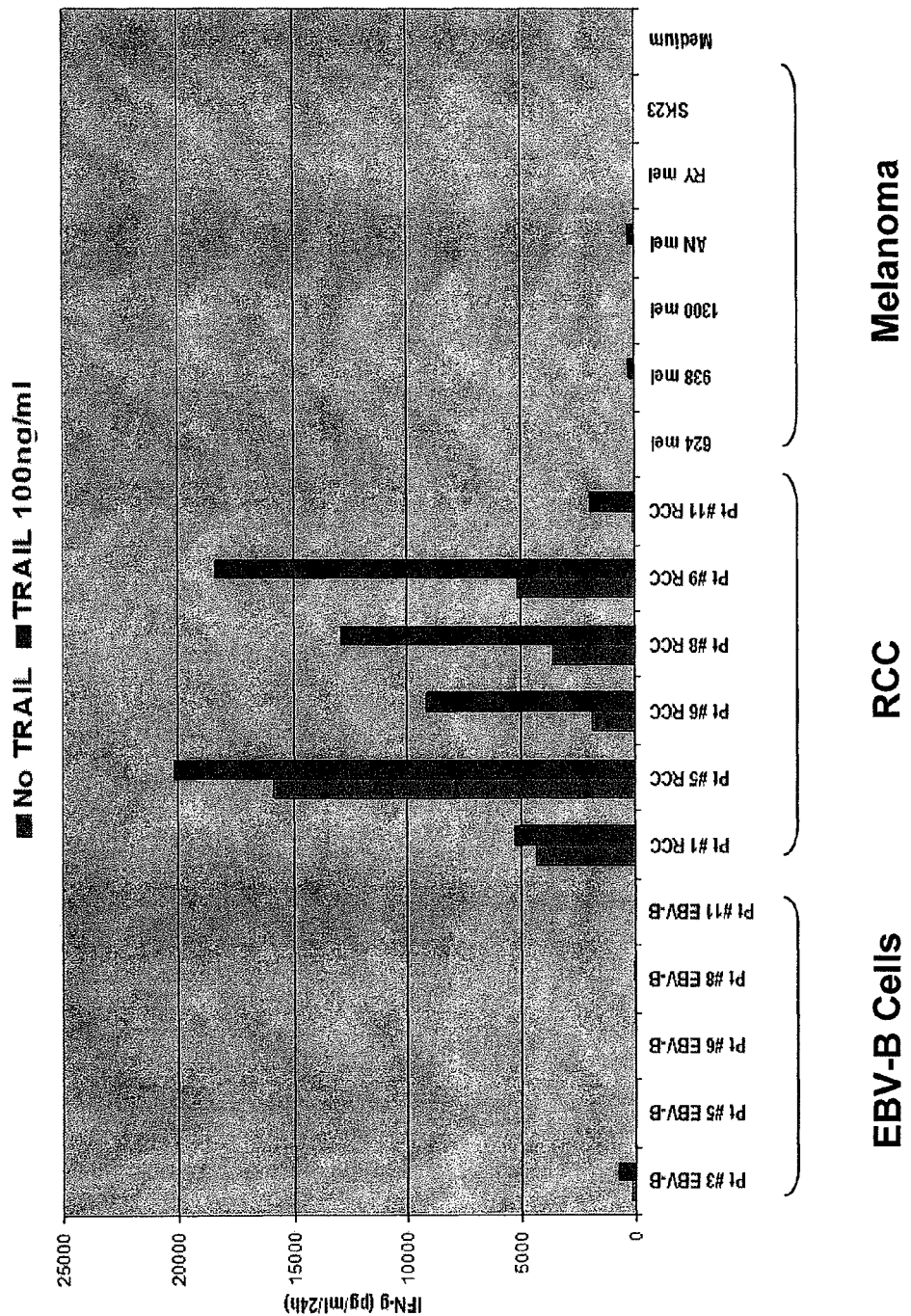

FIG. 8 is a graph of the IFN-γ secretion (pg/ml/24 h) by HC/2G-1 T-cell clones upon stimulation with EBV-Bs (EBV-B #3, #5, #6, #8, and #11), RCC #1 cells, RCC #6 cells, RCC #8 cells, RCC #9 cells, RCC #11, 624mel cells, 938mel cells, 1300mel cells, ANmel cells, RYmel cells, SK23 cells, or cultured in medium alone in the presence of exogenous TRAIL (right bars) or in the absence of exogenous TRAIL (left bars).

Figure 9:
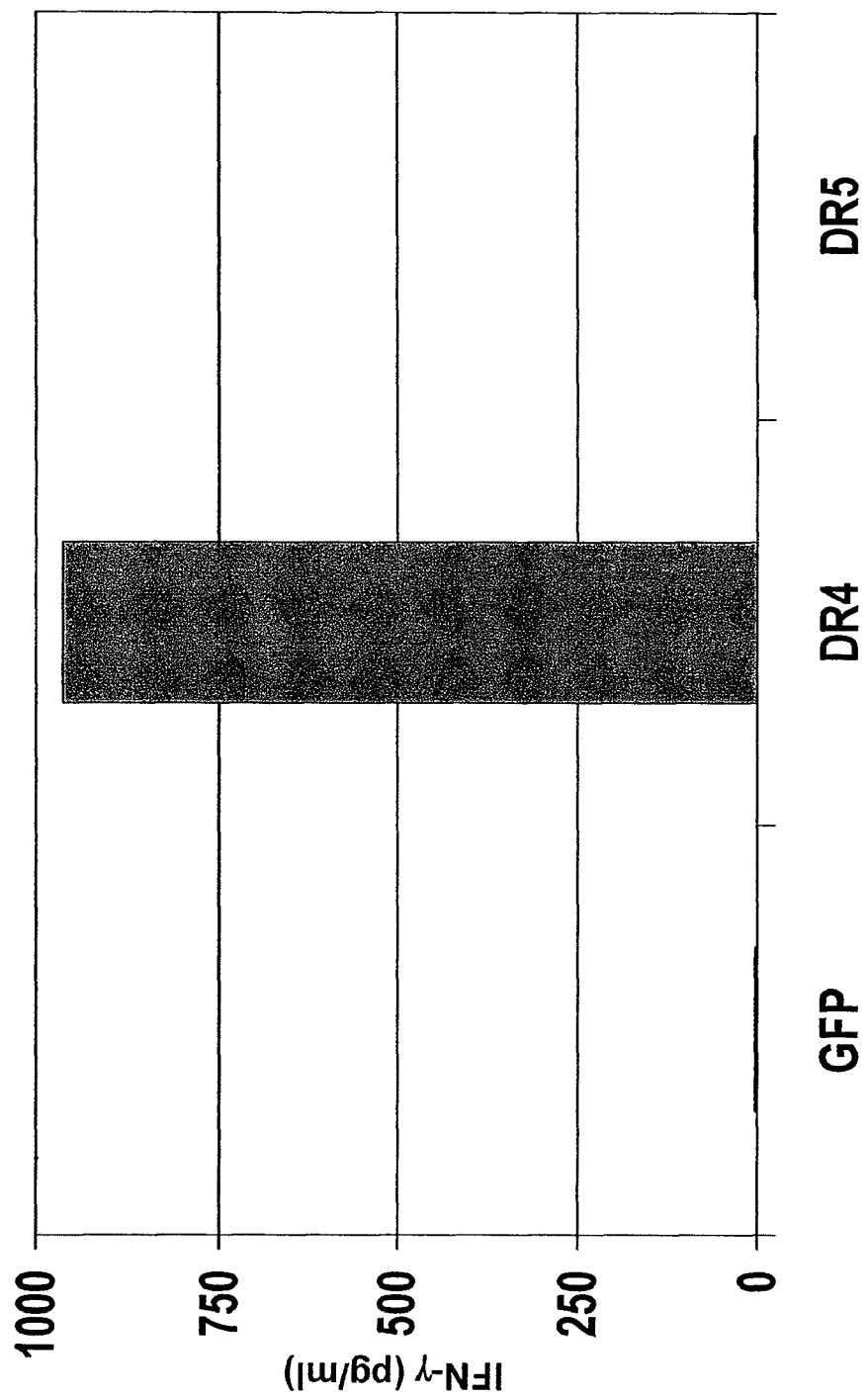

FIG. 9 is a graph of the IFN-γ secretion (pg/ml) by HC/2G-1 T-cell clones upon stimulation with HEK 293 transiently transduced with GFP, TRAIL-R1 (DR4) or TRAIL-R2 (DR5).

Figure 10:
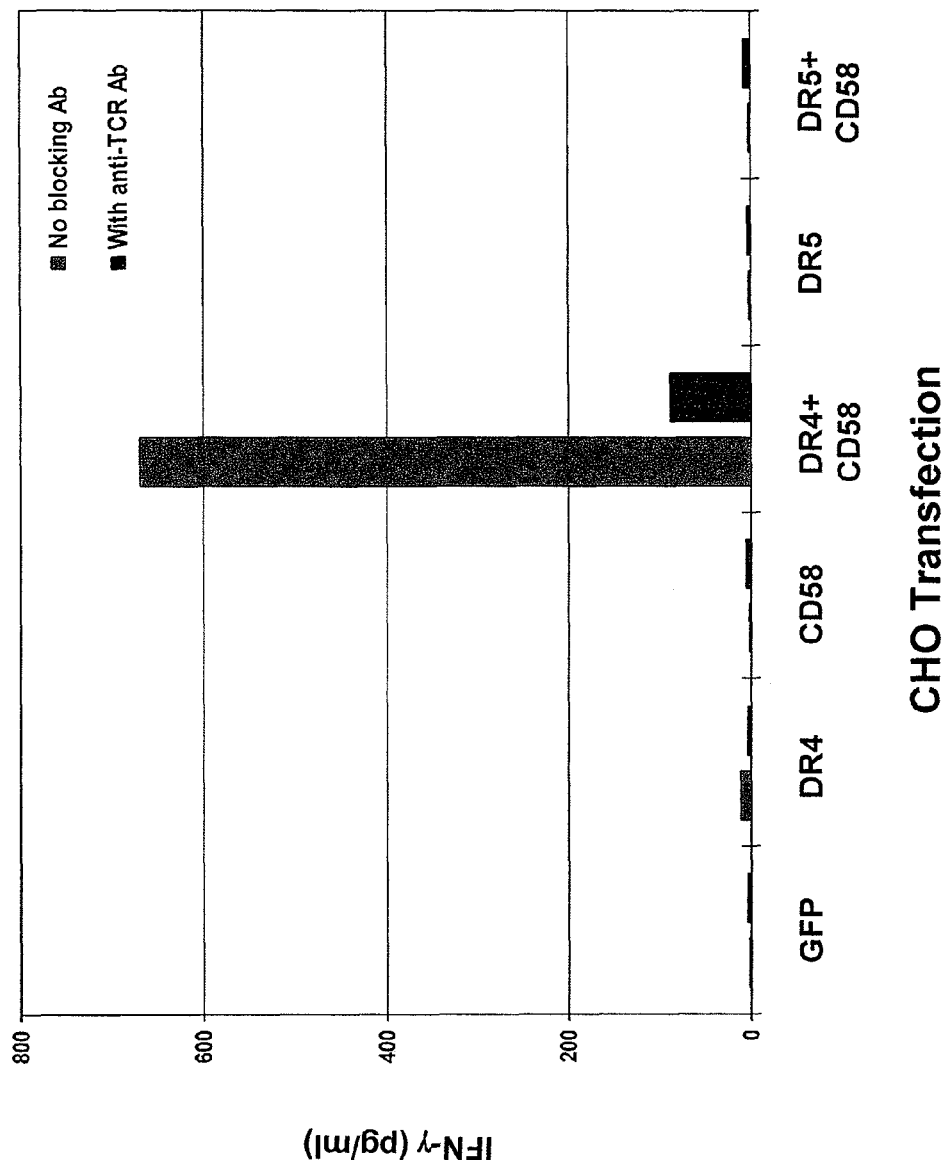

FIG. 10 is a graph of the IFN-γ secretion (pg/ml) by HC/2G-1 T-cell clones upon stimulation with Chinese hamster ovary (CHO) cells transduced with GFP, TRAIL-R1, CD58, TRAIL-R2, co-transduced with both TRAIL-R1 and CD58, or co-transduced with TRAIL-R2 and CD58 in the presence of anti-TCR Ab (right bars) or in the absence of antibody (left bars).

Figure 11:
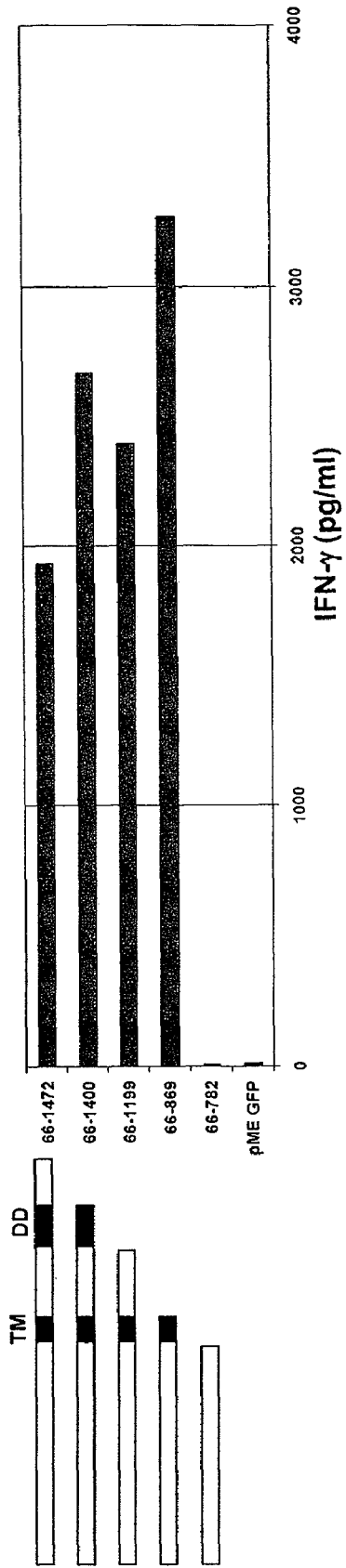

FIG. 11 is a graph of the IFN-γ secretion (pg/ml) by HC/2G-1 T-cell clones upon stimulation with CHO/CD58 cells transduced with TRAIL-R1 truncations including the extracellular and intracellular (including transmembrane domain (TM) and death domain (DD)) portions (66-1472), the extracellular portion and a part of the intracellular portion (including transmembrane domain (TM) and death domain (DD)) (66-1400), the extracellular portion, TM domain, and a part of the intracellular portion, but lacking the DD domain (66-1199), the extracellular portion but lacking the intracellular portion (i.e., lacking both the transmembrane domain (TM) and death domain (DD)) portions (66-869), and including the extracellular portion but lacking the entire intracellular portion (66-782), or pME GFP.

FIG. 12 is a graph of the IFN-γ secretion (pg/ml/24 h) by HC/2G-1 T-cell clones upon stimulation with RCC#6 or in the presence or absence of any or all of soluble TRAIL, plate-bound TRAIL-R1, and plate-bound anti-CD2 antibody.

DETAILED DESCRIPTION OF THE INVENTION

The invention provides an isolated or purified T cell receptor (TCR) having antigenic specificity for a cancer antigen, wherein the TCR recognizes the cancer antigen in a major histocompatibility complex (MHC)-independent manner. The inventive TCRs (and functional portions thereof) described herein include both substituted and unsubstituted TCRs (and functional portions thereof).

The phrase "having antigenic specificity" as used herein means that the TCR can specifically bind to and immunologically recognize the cancer antigen, such that binding of the TCR to the cancer antigen elicits an immune response.

The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. In a preferred embodiment of the invention, the cancer antigen is a kidney cancer antigen. In a more preferred embodiment, the cancer antigen is a renal cell carcinoma (RCC) antigen.

Without being bound to any particular theory, the inventive TCRs are able to recognize a cancer antigen in a major histocompatibility complex (MHC)-independent manner. By "major histocompatibility complex (MHC)-independent manner" as used herein means that the TCR, upon binding to the cancer antigen, can elicit an immune response in the absence of binding to a classical MHC molecule. The classical MHC molecule can be any classical MHC molecule known in the art, e.g., an MHC Class I molecule, an MHC Class II molecule, HLA-A molecules, HLA-B molecules, HLA-C molecules, HLA-DR molecules, HLA-DP molecules, etc. Classical MHC molecules are known in the art. The inventive TCR may, however, bind to the cancer antigen in a manner which requires a minor MHC molecule. For purposes herein, the minor MHC can be an HLA-E molecule, an HLA-G molecule, a CD1 molecule, e.g., CD1a, CD1b, CD1c, CD1d, etc.

Furthermore, without being bound to any particular theory, the inventive TCRs are able to recognize a cancer antigen in a CD8- and/or CD4-independent manner, which manner may be a result of the inventive TCRs being able to recognize a cancer antigen in an MHC-independent manner. By "CD8- and/or CD4-independent manner," is meant that the inventive TCRs, upon binding to a cancer antigen, can elicit an immune response in the absence of a CD8 or CD4 molecule, or both a CD8 and CD4 molecule, expressed on the cell expressing the inventive TCR or in the absence of a functional CD8 or CD4 molecule, or both. Unlike traditional TCRs, the inventive TCRs do not have a preference for CD8 or CD4 and can function in the context of either a CD8 or CD4 molecule.

Additionally, without being bound to any particular theory, it is believed that the inventive TCRs recognize soluble TRAIL presented by death receptors, e.g., TRAIL-R1 (DR4), which are frequently displayed by human tumors. TRAIL is a protein consisting of 281 amino acids, and has also been referred to as APO-2L. Five TRAIL receptors have been identified, and can be divided into two categories: death receptors (TRAIL-R1 and TRAIL-R2, which are capable of inducing apoptosis), and decoy receptors, (TRAIL-R3 and TRAIL-R5, that lack the death domain, and TRAIL-R4, which contains a truncated non-functional death domain). TRAIL-R5 is secreted to the extracellular fluid.

TRAIL's death receptors (TRAIL-R1 and TRAIL R2) are mainly expressed in transformed cells, while its decoy receptors (TRAIL-R3, TRAIL-R4, and TRAIL-R5) are expressed in normal cells.

The invention provides a TCR comprising two polypeptides (i.e., polypeptide chains), such as an α chain of a TCR, a β chain of a TCR, a γ chain of a TCR, a δ chain of a TCR, or a combination thereof. Such polypeptides chains of TCRs are known in the art. The polypeptides of the inventive TCR can comprise any amino acid sequence, provided that the TCR has antigenic specificity for a cancer antigen and can recognize the cancer antigen in an MHC-independent manner.

In a preferred embodiment of the invention, the TCR comprises two polypeptide chains, each of which comprises a variable region comprising a complementarity determining region (CDR) 1, a CDR2, and a CDR3 of a TCR. Preferably, the first polypeptide chain comprises a CDR1 comprising the amino acid sequence of SEQ ID NO: 16 (CDR1 of α chain), a CDR2 comprising the amino acid sequence of SEQ ID NO: 17 (CDR2 of α chain), and a CDR3 comprising the amino acid sequence of SEQ ID NO: 18 (CDR3 of α chain), and the second polypeptide chain comprises a CDR1 comprising the amino acid sequence of SEQ ID NO: 19 (CDR1 of β chain), a CDR2 comprising the amino acid sequence of SEQ ID NO: 20 (CDR2 of β chain), and a CDR3 comprising the amino acid sequence of SEQ ID NO: 21 (CDR3 of β chain). In this regard, the inventive TCR can comprise the amino acid sequences selected from the group consisting of SEQ ID NOs: 16-18, 19-21, and 16-21. Preferably the TCR comprises the amino acid sequences of SEQ ID NOs: 16-21.

Alternatively or additionally, the TCR can comprise an amino acid sequence of a variable region of a TCR comprising the CDRs set forth above. In this regard, the TCR can comprise the amino acid sequence of SEQ ID NO: 7 (the variable region of an α chain) or 8 (the variable region of a β chain), or both SEQ ID NOs: 7 and 8. Preferably, the inventive TCR comprises the amino acid sequences of SEQ ID NOs: 7 and 8.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of an α chain as set forth above. In this regard, the inventive TCR can comprise the amino acid sequence of SEQ ID NO: 3. An inventive TCR of this type can be paired with any β chain of a TCR. Preferably, the β chain of the inventive TCR comprises the variable region of a β chain as set forth above. In this regard, the inventive TCR can comprise the amino acid sequence of SEQ ID NO: 4. The inventive TCR, therefore, can comprise the amino acid sequence of SEQ ID NO: 3 or 4, or both SEQ ID NOs: 3 and 4. Preferably, the inventive TCR comprises the amino acid sequences of SEQ ID NOs: 3 and 4.

The invention also provides substituted amino acid sequences that encode TCRs (or functional portions thereof). In some embodiments, the substituted TCRs (or functional portions thereof) provide an increased specificity for a cancer antigen as compared to an unsubstituted amino acid sequence. In general, the substituted amino acid sequences SEQ ID NOs:22-23 and SEQ ID NO:26-29 correspond with all or portions of the native, unsubstituted SEQ ID NO:3 (TCR α chain), with SEQ ID NOs:22-23 and SEQ ID NO:26-29 having at least one substitution when compared to SEQ ID NO:3. Preferably, either or both of the native Tyr117 and Ser119 of SEQ ID NO:3 is substituted.

In particular, the invention provides an isolated or purified TCR comprising an amino acid sequence selected from the group consisting of SEQ ID NO:28, wherein Xaa7 is selected from the group consisting of Lys and Ala; and SEQ ID NO:29, wherein Xaa5 is Phe and Xaa7 is selected from the group consisting of Lys, Ala, and Ser. SEQ ID NO:28 generally corresponds to positions 113-125 of the native, unsubstituted SEQ ID NO:3 with the exception that in SEQ ID NO:28, Ser7 is substituted. SEQ ID NO:29 generally corresponds to positions 113-125 of the native, unsubstituted SEQ ID NO:3 with the exception that in SEQ ID NO:29, Tyr5 is substituted and Ser7 is substituted or unsubstituted.

The invention also provides an isolated or purified TCR comprising an amino acid sequence selected from the group consisting of SEQ ID NO:26, wherein Xaa119 is selected from the group consisting of Lys and Ala; and SEQ ID NO:27, wherein Xaa117 is Phe and Xaa119 is selected from the group consisting of Lys, Ala, and Ser. SEQ ID NO:26 generally corresponds to positions 1-125 of the native, unsubstituted SEQ ID NO:3 with the exception that in SEQ ID NO:26, Ser119 is substituted. SEQ ID NO:27 generally corresponds to positions 1-125 of the native, unsubstituted SEQ ID NO:3 with the exception that in SEQ ID NO:27, Tyr117 is substituted and Ser119 is substituted or unsubstituted.

Also provided by the invention is an isolated or purified TCR comprising an amino acid sequence selected from the group consisting of SEQ ID NO:22, wherein Xaa119 is selected from the group consisting of Lys and Ala; and SEQ ID NO:23, wherein Xaa117 is Phe and Xaa119 is selected from the group consisting of Lys, Ala, and Ser. SEQ ID NO:22 generally corresponds to the native, unsubstituted SEQ ID NO:3 with the exception that in SEQ ID NO:22, Ser119 is substituted. SEQ ID NO:23 generally corresponds to the native, unsubstituted SEQ ID NO:3 with the exception that in SEQ ID NO:23, Tyr117 is substituted and Ser119 is substituted or unsubstituted.

Like the first embodiment of the TCRs of the invention, the substituted TCR comprises two polypeptide chains, each of which comprises a variable region comprising a complementarity determining region (CDR) 1, a CDR2, and a CDR3 of a TCR. Preferably, the first polypeptide chain comprises a CDR1 comprising the amino acid sequence of SEQ ID NO: 16 (CDR1 of α chain), a CDR2 comprising the amino acid sequence of SEQ ID NO: 17 (CDR2 of α chain), and a substituted CDR3 comprising the amino acid sequence of SEQ ID NO: 28 or SEQ ID NO: 29 (substituted CDR3 of α chain), and the second polypeptide chain comprises a CDR1 comprising the amino acid sequence of SEQ ID NO: 19 (CDR1 of β chain), a CDR2 comprising the amino acid sequence of SEQ ID NO: 20 (CDR2 of β chain), and a CDR3 comprising the amino acid sequence of SEQ ID NO: 21 (CDR3 of β chain). In this regard, the inventive substituted TCR can comprise the amino acid sequences selected from the group consisting of SEQ ID NOs: 16-17 and 28; 16-17 and 29; 19-21; 16-17, 28 and 19-21; and 16-17, 29 and 19-21. Preferably the substituted TCR comprises the amino acid sequences of SEQ ID NOs: 16-17, 19-21, and 28 or SEQ ID NOs: 16-17, 19-21, and 29.

Alternatively or additionally, the substituted TCR can comprise a substituted amino acid sequence of a variable region of a TCR comprising the CDRs set forth above. In this regard, the TCR can comprise the substituted amino acid sequence of SEQ ID NO: 26 (the substituted variable region of an α chain) or 8 (the variable region of a β chain), or both SEQ ID NOs: 26 and 8. In other embodiments, the TCR can comprise the substituted amino acid sequence of SEQ ID NO: 27 (the substituted variable region of an α chain) or 8 (the variable region of a β chain), or both SEQ ID NOs: 27 and 8. Preferably, the inventive TCR comprises the amino acid sequences of SEQ ID NOs: 26 and 8 or SEQ ID NOs: 27 and 8.

Alternatively or additionally, the substituted TCR can comprise a substituted α chain of a TCR and a β chain of a TCR. Each of the α chain and β chain of the inventive TCR can independently comprise any amino acid sequence. Preferably, the substituted α chain comprises a substituted variable region of an α chain as set forth above. In this regard, the inventive substituted α chain of the TCR can comprise the amino acid sequence of SEQ ID NO: 22 or 23. An inventive substituted a chain of this type can be paired with any β chain of a TCR. Preferably, the β chain of the inventive TCR comprises the variable region of a β chain as set forth above. In this regard, the inventive TCR can comprise the amino acid sequence of SEQ ID NO: 4. The inventive TCR, therefore, can comprise the amino acid sequence of SEQ ID NO: 22, 23 or 4, both SEQ ID NOs: 23 and 4, or both SEQ ID NOs: 22 and 4. Preferably, the inventive TCR comprises the amino acid sequences of SEQ ID NOs: 23 and 4 or SEQ ID NOs: 22 and 4.

Also provided by the invention is an isolated or purified polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to the cancer antigen. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to the cancer antigen (e.g., in an MHC-independent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to a cancer antigen in an MHC-independent manner, having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In this regard, the polypeptide can comprise a functional portion comprising the amino acid sequence of SEQ ID NO: 16 (CDR1 of α chain), 17 (CDR2 of α chain), 18 (CDR3 of α chain), 19 (CDR1 of β chain), 20 (CDR2 of β chain), 21 (CDR3 of β chain), 28 (substituted CDR3 of α chain), 29 (substituted CDR3 of α chain), or a combination thereof. Preferably, the inventive unsubstituted polypeptide comprises a functional portion comprising SEQ ID NOs: 16-18, 19-21, or all of SEQ ID NOs: 16-21. More preferably, the unsubstituted polypeptide comprises a functional portion comprising the amino acid sequences of SEQ ID NOs: 16-21. Preferably, the inventive substituted polypeptide comprises a functional portion comprising SEQ ID NOs: 16-17 and 28; 16-17 and 29; 19-21; all of SEQ ID NOs: 16-17, 19-21 and 28; or all of SEQ ID NOs: 16-17, 19-21 and 29. More preferably, the substituted polypeptide comprises a functional portion comprising the amino acid sequences of SEQ ID NOs: 16-17, 19-21 and 28 or SEQ ID NOs: 16-17, 19-21 and 29.

Alternatively or additionally, the inventive polypeptide can comprise, for instance, the variable region of the inventive TCR comprising a combination of the CDR regions set forth above. In this regard, the TCR can comprise the amino acid sequence of SEQ ID NO: 7 (the variable region of an α chain), 8 (the variable region of a β chain), 26 (the substituted variable region of an α chain), 27 (the substituted variable region of an α chain), both SEQ ID NOs: 7 and 8, both SEQ ID NOs: 26 and 8, or both SEQ ID NOs: 27 and 8. Preferably, the polypeptide comprises the amino acid sequence of SEQ ID NO: 8 or the amino acid sequences of SEQ ID NOs: 7 and 8. Preferably, the substituted polypeptide comprises the amino acid sequences of SEQ ID NOs: 26 and 8 or SEQ ID NOs: 27 and 8.

Alternatively or additionally, the inventive polypeptide can comprise the entire length of an α or β chain of one of the TCRs described herein. In this regard, the inventive polypeptide can comprise an amino acid sequence of SEQ ID NOs: 3, 4, 22, or 23. Alternatively, the polypeptide of the invention can comprise α and β chains of the TCRs described herein. For example, the inventive polypeptide can comprise both amino acid sequences of SEQ ID NOs: 3 and 4, both SEQ ID NOs: 22 and 4, or both SEQ ID NOs: 23 and 4.

The invention further provides an isolated or purified protein comprising at least one of the polypeptides described herein. By "protein" is meant a molecule comprising one or more polypeptide chains.

The protein of the invention can comprise a first polypeptide chain comprising the amino acid sequence of SEQ ID NO: 7, 26, or 27 and a second polypeptide chain comprising the amino acid sequence of SEQ ID NO: 8. The protein of the invention can, for example, comprise a first polypeptide chain comprising the amino acid sequence of SEQ ID NO: 3, 22, or 23 and a second polypeptide chain comprising the amino acid sequence of SEQ ID NO: 4. In this instance, the protein of the invention can be a TCR. Alternatively, if, for example, the protein comprises a single polypeptide chain comprising SEQ ID NO: 3, 22, or 23 and SEQ ID NO: 4, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to the cancer antigen for which the parent TCR has antigenic specificity or to which the parent polypeptide or protein specifically binds (e.g., in an MHC-independent manner), to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 98% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the functional variant, e.g., other amino acids, do not materially change the biological activity of the functional variant. In this regard, the inventive TCR, polypeptide, or protein can, for example, consist essentially of the amino acid sequence of SEQ ID NO: 3, 22, 23, or 4, both SEQ ID NOs: 3 and 4, both SEQ ID NOs: 22 and 4, or both SEQ ID NOs: 23 and 4. Also, for instance, the inventive TCRs, polypeptides, or proteins can consist essentially of the amino acid sequence(s) of SEQ ID NO: 7, 26, 27, or 8, both SEQ ID NOs: 7 and 8, both SEQ ID NOs: 26 and 8, both SEQ ID NOs: 27 and 8. Furthermore, the inventive TCRs, polypeptides, or proteins can consist essentially of the amino acid sequence of SEQ ID NO: 16 (CDR1 of α chain), 17 (CDR2 of α chain), 18 (CDR3 of α chain), 19 (CDR1 of β chain), 20 (CDR2 of β chain), 21 (CDR3 of β chain), 28 (substituted CDR3 of α chain), 29 (substituted CDR3 of α chain), or any combination thereof, e.g., SEQ ID NOs: 16-18; 19-21; 16-21; 16-17, 28 and 19-21; 16-17, 29 and 19-21.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to a cancer antigen in an MHC-independent manner, detect cancer in a host, or treat or prevent cancer in a host, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Further provided by the invention is a nucleic acid comprising a nucleotide sequence encoding any of the TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins, or functional portions or functional variants thereof. For example, the nucleic acid can comprise a nucleotide sequence comprising SEQ ID NO: 1, 2, 5, or 6, both SEQ ID NOs: 1 and 2, or both SEQ ID NOs: 5 and 6. The nucleotide sequence alternatively can comprise a nucleotide sequence which is degenerate to SEQ ID NO: 1, 2, 5, or 6, or which comprises a nucleotide sequence comprising a nucleotide sequence degenerate to SEQ ID NO: 1 and a nucleotide sequence degenerate to SEQ ID NO: 2 or comprising a nucleotide sequence degenerate to SEQ ID NO: 5 and a nucleotide sequence degenerate to SEQ ID NO: 6. Preferably, the nucleic acid comprises a nucleotide sequence comprising SEQ ID NO: 1, 2, or 6, SEQ ID NOs: 1 and 2, or SEQ ID NOs: 5 and 6, or a nucleotide sequence which is degenerate thereto.

The invention also provides substituted nucleic acid sequences which encode any of the substituted TCRs, substituted polypeptides, substituted proteins, or substituted functional portions or functional variants thereof.

In one embodiment, the nucleic acid comprises an isolated or purified nucleic acid selected from the group consisting of a) SEQ ID NO:32, wherein NNN at positions 13-15 is a codon that encodes Phe and wherein NNN at positions 19-21 is a codon that encodes Lys; b) SEQ ID NO:35, wherein NNN at positions 19-21 is a codon that encodes an amino acid selected from the group consisting of Lys and Ala; and c) SEQ ID NO:36, wherein NNN at positions 13-15 is a codon that encodes Phe and wherein NNN at positions 19-21 is a codon that encodes an amino acid selected from the group consisting of Lys, Ala, and Ser.

In another embodiment, the nucleic acid comprises an isolated or purified nucleic acid comprising a nucleic acid sequence selected from the group consisting of a) SEQ ID NO:31, wherein NNN at positions 349-351 is a codon that encodes Phe and wherein NNN at positions 355-357 is a codon that encodes Lys; b) SEQ ID NO:33, wherein NNN at positions 355-357 is a codon that encodes an amino acid selected from the group consisting of Lys and Ala; and c) SEQ ID NO:34, wherein NNN at positions 349-351 is a codon that encodes Phe and wherein NNN at positions 355-357 is a codon that encodes an amino acid selected from the group consisting of Lys, Ala, and Ser.

In still another embodiment, the nucleic acid comprises an isolated or purified nucleic acid comprising a nucleic acid sequence selected from the group consisting of a) SEQ ID NO:30, wherein NNN at positions 349-351 is a codon that encodes Phe and wherein NNN at positions 355-357 is a codon that encodes Lys; b) SEQ ID NO:24, wherein NNN at positions 355-357 is a codon that encodes an amino acid selected from the group consisting of Lys and Ala; and c) SEQ ID NO:25, wherein NNN at positions 349-351 is a codon that encodes Phe and wherein NNN at positions 355-357 is a codon that encodes an amino acid selected from the group consisting of Lys, Ala, and Ser.

The codons of the substituted nucleic acids of the invention that encode any of Lys, Ala, Ser, and Phe may be any suitable codon that encodes Lys, Ala, Ser, and Phe, respectively. For example, the codons may be any of those set forth in Table 1 below.

TABLE 1

Amino Acids and Corresponding Codons

| Amino Acid | Codon |
| --- | --- |
| Phe | TTC TTT |
| Ser | AGT AGC TCA TCC TCG TCT |
| Ala | GCT GCA GCC GCG |
| Lys | AAA AAG |

Preferably, the codon that encodes Lys is AAG and the codon that encodes Ala is GCC.

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency. SEQ ID NOs: 30-32 are optimized nucleic acid sequences.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell.

Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), peripheral blood mononuclear cells (PBMCs), peripheral blood leukocytes (PBLs), tumor infiltrating cells (TILs), memory T cells, naïve T cells, and the like. Preferably, the T cell is a $CD8^+$ T cell or a $CD4^+$ T cell.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs described herein. Preferably, the functional portion specifically binds to the cancer antigen, e.g., the functional portion comprising the amino acid sequence SEQ ID NO: 16 (CDR1 of α chain), 17 (CDR2 of α chain), 18 (CDR3 of α chain), 19 (CDR1 of β chain), 20 (CDR2 of β chain), 21 (CDR3 of β chain), 28 (substituted CDR3 of α chain), 29 (substituted CDR3 of α chain), SEQ ID NO: 7, SEQ ID NO: 8, SEQ ID NO:26, SEQ ID NO: 27, or a combination thereof, e.g., 16-18; 19-21; 16-21; 16-17 and 28; 16-17 and 29; 16-17, 28, and 19-21; and 16-17, 29, and 19-21. More preferably, the functional portion comprises the amino acid sequences of SEQ ID NOs: 16-21; 16-17, 28, and 19-21; or 16-17, 29, and 19-21. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The inventive TCRs, polypeptides, proteins (including functional portions and variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive TCR materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can consist of (a) liquid solutions, such as an effective amount of the inventive TCR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive TCR material in a flavor, usually sucrose and acacia or tragacanth, as well as pastilles comprising the inventive TCR material in an inert base, such as gelatin and glycerin, or sucrose and acacia, emulsions, gels, and the like containing, in addition to, such excipients as are known in the art.

The inventive TCR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

Additionally, the inventive TCR materials, or compositions comprising such inventive TCR materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art, including, for instance, the methods described herein as Example 1.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a linker to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the inventive TCR materials to the targeting moiety. One of ordinary skill in the art recognizes that sites on the inventive TCR materials, which are not necessary for the function of the inventive TCR materials, are ideal sites for attaching a linker and/or a targeting moiety, provided that the linker and/or targeting moiety, once attached to the inventive TCR materials, do(es) not interfere with the function of the inventive TCR materials, i.e., the ability to bind to a cancer antigen, or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive pharmaceutical compositions, TCRs, polypeptides, proteins, nucleic acids, recombinant expression vectors, host cells, or populations of cells can be used in methods of treating or preventing cancer. Without being bound to a particular theory, the inventive TCRs are believed to bind specifically to a cancer antigen, e.g., a renal cell carcinoma antigen, such that the TCR (or related inventive polypeptide or protein) when expressed by a cell is able to mediate an immune response against the cell expressing the cancer antigen. In this regard, the invention provides a method of treating or preventing cancer in a host, comprising administering to the host any of the TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the host.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a host. The method comprises (i) contacting a sample comprising cells of the cancer any of the inventive TCRs, polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of cancer in the host.

With respect to the inventive method of detecting cancer in a host, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting step can take place in vitro or in vivo with respect to the host. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is kidney cancer. More preferably, the cancer is RCC.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

The following examples further illustrate the invention but, of course, should not be construed as in any way limiting its scope.

The following cell lines and antibodies were used in the examples described herein:

Tumor lines from renal cell carcinoma (RCC) patients and Epstein-Barr virus-transformed B cells (EBV-Bs) were established as described previously (Wang et al., *J. Immunother.* 28: 551-559 (2005)). RCC lines were maintained in Dulbecco's Modified Eagle Medium (DMEM; Invitrogen Life Technologies, Gaithersburg, Md., USA) supplemented with 10% fetal bovine serum (FBS; Invitrogen Life Technologies). EBV-B cells were maintained in RPMI 1640 (Life Technologies) containing 10% FBS. Tumor lines, which were used as controls in the experiments, were obtained from the laboratories of the Surgery Branch of the National Cancer Institute (Bethesda, Md., USA), and maintained in RPMI 1640 supplemented with 10% FBS. Human primary renal epithelial cells were either purchased from Cambrex Bioscience (Walkersville, Md., USA) or gifts from Dr. Scott Garrett (University of North Dakota, Grand Forks, N.D., USA).

For immunophenotyping, monoclonal antibodies (MoAbs), including fluorescein isothiocyanate (FITC)-labeled anti-human IgG isotypes, anti-CD3, anti-CD4, anti-CD8, anti-CD16, anti-CD57, and anti-TCRγ/δ, and phycoerytherin (PE)-labeled anti-human IgG isotypes, anti-CD3, anti-CD4, anti-CD8, anti-TCRα/β, anti-CD56, and anti-CD161 were purchased from BD Pharmingen (San Jose, Calif., USA). PE-labeled anti-Vβ2 antibodies were purchased from Beckman Coulter (Miami, Fla., USA).

For blocking experiments, W6/32 (anti-pan HLA class I) and IVA12 (anti-pan HLA class II) were kind gifts of Dr. Paul Robbins (National Cancer Institute). Purified anti-human TCRα/β antibody was purchased from BD Pharmingen.

Example 1

This example demonstrates a method of making a T cell clone having antigenic specificity for a renal cell carcinoma antigen and demonstrates the biological activity of that clone.

To establish RCC-specific T cells, CD8+- and/or CD4+-enriched T cells (Miltenyi Biotec Inc, Auburn, Calif.) were stimulated with Day 6 dendritic cells (DCs) co-cultured with UV-irradiated autologous tumor cells, as described previously with some modifications (Wang et al., 2005, supra). Briefly, CD 14+ DCs were isolated from patient peripheral blood mononuclear cells (PBMC) using CD14 microbeads according to the manufacturer's instructions (Miltenyi Biotec Inc. Auburn, Calif.), and cultured in RPMI 1640 supplemented with 10% human serum (HS; Valley Biomedical Inc. Winchester, Va.), GM-CSF (1000 U/ml; Peprotech, Rocky Hill, N.J.), and IL-4 (1000 U/ml; Peprotech) for 6 days to generate monocyte-derived DCs (herein referred to as Day 6 DCs). To stimulate T cells, Day 6 DCs were co-cultured with UV-irradiated tumor cells (UVB; 312 mm; Spectroline, Westbury, N.Y.) at 1:1 ratio in RPMI 1640 supplemented with 10% HS in the presence of GM-CSF, IL-4, and IFN-γ (1000 U/ml each); Pierce Biotechnology, Inc. Rockford, Ill., USA) overnight in 96-well round-bottom plates. On the next day, the DC-tumor co-culture plates were replenished with fresh RPMI 1640 supplemented with 10% HS, GM-CSF, and IL-4. CD8+-enriched T cells (Miltenyi CD8+Cell Isolation Kit II) and CD4+-enriched, CD25-depleted T cells (Miltenyi CD4+ Cell Isolation Kit II and CD25 microbeads) were isolated and added to DC-tumor co-culture in RPMI supplemented with 10% HS, IL-2 (120 IU/ml), and CD40L (500 ng/ml; Immunex, Seattle, Wash., USA). Seven days later, T cells were re-stimulated once by transferring them to a second identically prepared DC-tumor culture. Testing the T cells for IFN-γ production upon co-culturing with autologous EBV-B or RCC cells occurred 7 days after restimulation. Microwells, which had an IFN-γ concentration of at least 100 pg/ml when co-cultured with autologous renal tumor (RCC #1) cells and twice that when co-cultured with autologous EBV-B cells (EBV-B #1), were deemed as positive. T cell clones were derived from the cultures of these positive microwells by limiting dilution, and expanded, when the clones were positive for IFN-γ secretion upon co-culturing with autologous EBV tumor cells.

As shown in FIG. 1A, T cells from Microwell HC/2G that met the criteria of having an IFN-γ concentration of at least 100 pg/ml and twice that of a co-culture with EBV-B cells.

T cell clone HC/2G-1 was derived from Microwell HC/2G by plating 1 cell per well in a limiting dilution assay. HC/2G-1 ($1 \times 10^4$ cells/well) was co-cultured with a panel of HLA-mismatched renal tumors, EBV-Bs, melanoma tumors, other tumor lines, normal human epithelial lines and fibroblasts overnight and tested for IFN-γ secretion by ELISA. As shown in FIG. 1B, T cell clone HC/2G-1 secreted IFN-γ when stimulated with multiple HLA mismatched renal tumors.

A standard 4-hour 51Cr-release assay was performed to test the cytotoxicity of T cells against tumors. Briefly, target cells were labeled for 1 h at 37° C. with 51Cr (200 μCi; Amersham Biosciences; Piscataway, N.J.). Labeled target cells were then washed three times and plated in triplicate at a concentration of 1×10$^4$ per well in 96-well round-bottom plates. Effector cells (HC/2G-1 T cell clones) were prepared and added to target cells at various E:T ratios. After a 4-hour incubation, the supernatant was harvested and counted on a Wallac 1470 Wizard automatic gamma counter. Maximum 51Cr release was determined by adding 2% SDS to the target cells, and spontaneous 51Cr release was determined by adding medium to the target cells. The percentage of specific lysis was calculated as follows: [(experimental cpm−spontaneous cpm)/(maximum cpm−spontaneous cpm)]×100.

Figure 1C:
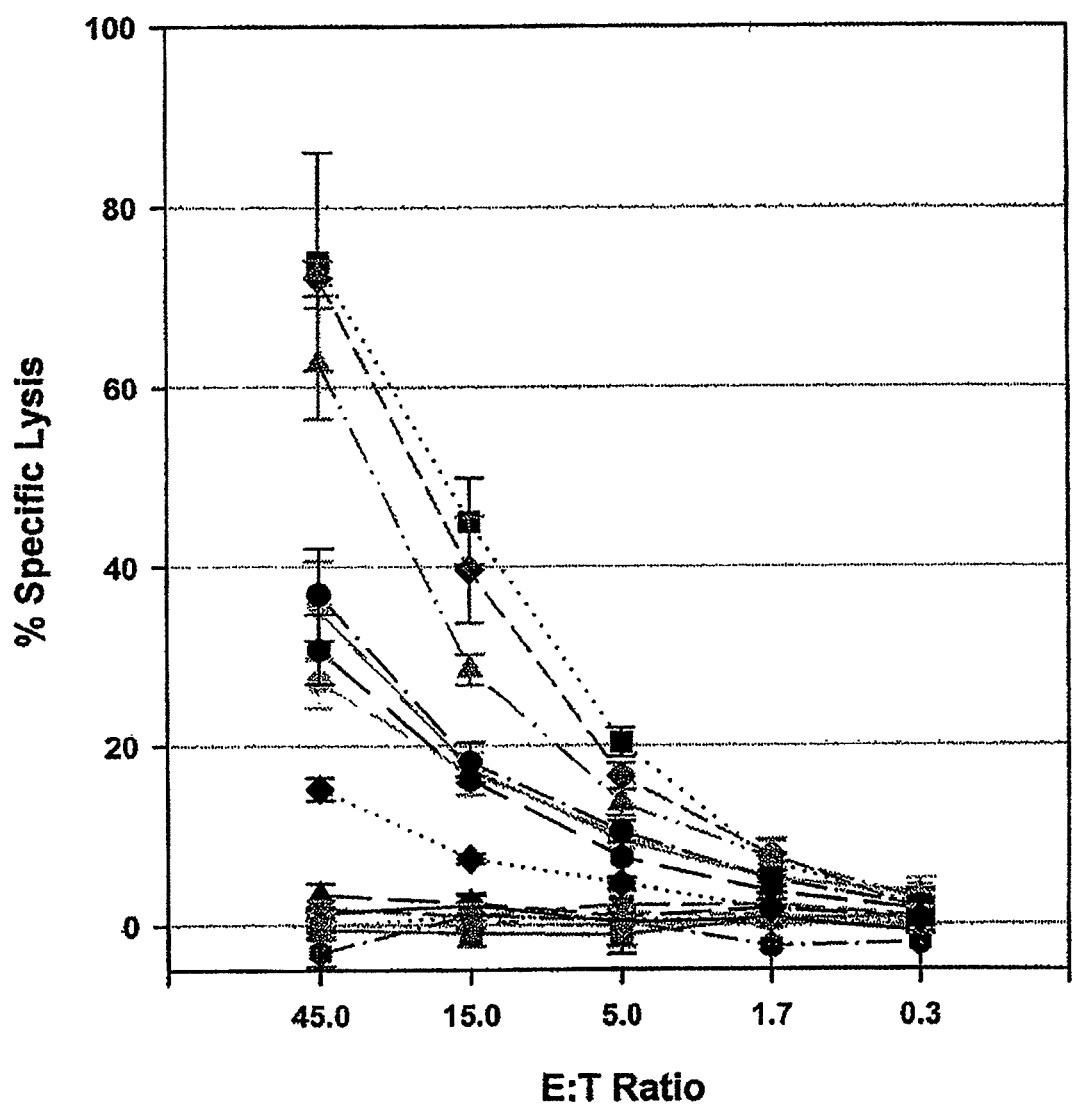

As shown in FIG. 1C, T cell clone HC/2G-1 lysed multiple HLA mismatched renal tumors. Specifically, RCC #1, 2, and 5-10 cells were lysed by the T cell clones.

This example demonstrated a method of making a T cell clone specific for a renal cell carcinoma antigen. This example further demonstrated that the T cell clone HC/2G-1 recognized a majority of renal tumors.

Example 2

This example demonstrates a characterization of T cell clone HC/2G1.

Figure 2A:
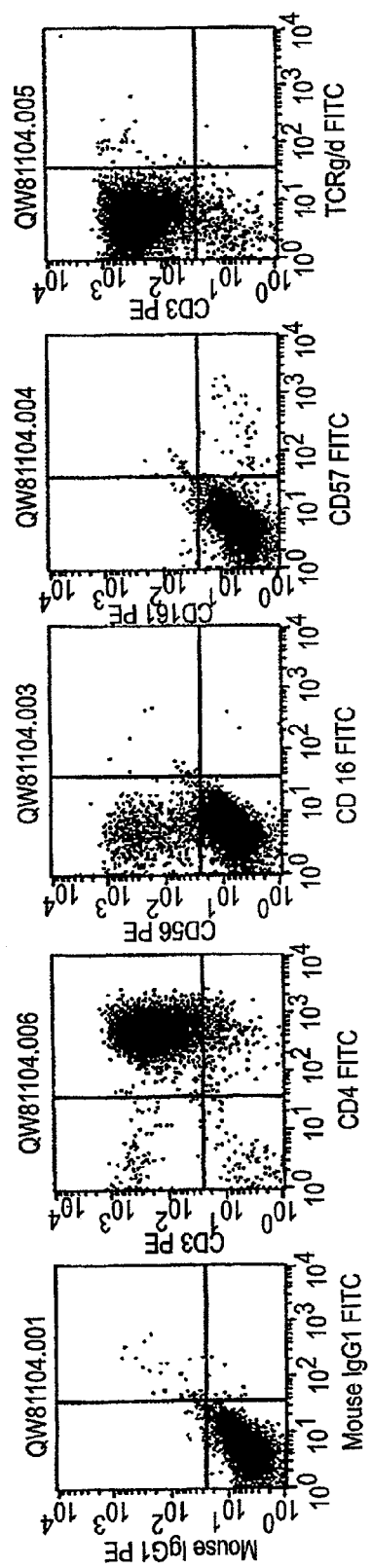
FIG. 2B is a graph of the cytokine secretion (IL-1Ra, IL-3, IL-4, IL-5, IL-10, IL-13, IL-17, IL-18, and GMCSF) of HC/2G-1 T cell clones upon stimulation with EBV-B #1 (solid bars), RCC #1 (diagonal lined bars), EBV #11 (crisscrossed bars), and RCC #11 (vertical lined bars) cells.

HC/2G-1 T cell clones were stained with the FITC- and PE-labeled anti-human MoAbs described above, and analyzed by FACScan. As shown in FIGS. 2A and 3A, the T cell clones were positive for expression of TCR α and β chains, CD3, CD4, and CD56 and negative for expression of CD16, CD57, CD161, and TCR γ and δ chains.

HC/2G-1 T cell clones (1×10$^4$ per well) were co-cultured with autologous tumor cells (RCC#1 and EBV-B#1) or allogeneic tumor cells (RCC#11 and EBV-B #11) overnight, and the supernatant was collected and tested for cytokine secretion by SearchLight™ (Pierce Biotechnology, Inc., Rockford, Ill.). As a control, HC/2G-1, EBV-Bs and RCCs cultured alone were also included in the assay. As shown in FIG. 2B, HC/2G-1 T cell clones secreted multiple cytokines upon stimulation with autologous RCC cells. In contrast, HC/2G-1, EBV-Bs and RCCs cultured alone showed no or very little cytokine secretion (data not shown).

Example 3

This example demonstrates that the activity of HC/2G-1 T cell clones was mediated through the TCR and was independent of MHC molecules of HLA Class I and HLA Class II.

Autologous RCC cells (RCC#1; 5×104 cells in 100 μl) were incubated with each blocking mAb (anti-HLA class I, anti-HLA class II, anti-TCRα/β and anti-CD4) at the concentration of 10 μg/ml for 30 min at 37° C. in a flat-bottom 96-well plate. HC/2G-1 T cells (1 to 5×10$^4$ cells/well) were then added and incubated with target cells overnight at 37° C. As a control, HLA-B44-restricted CTL clone (MW/5H-5) and HLA-class II-restricted CD4$^+$ T cell clone (HC/10C-3) were co-cultured with their autologous tumors. The supernatants were harvested and assayed for IFN-γ concentration by ELISA.

As shown in FIG. 3B, the reactivity of HC/2G-1 T cell clones was blocked by anti-TCR antibodies, not blocked by anti-HLA Class II antibodies, and partially blocked by anti-HLA Class I antibodies. In contrast, the anti-HLA Class I antibodies blocked the activity of MW/5H-5 cells, and the anti-HLA Class II antibodies effectively blocked the activity of HC/10C-3 cells, as expected.

This example demonstrated that the T cell clone HC/2G-1 acts through its TCR and in an MHC-independent manner.

Example 4

This example demonstrates a method of producing allogeneic cells expressing the TCR of HC/2G-1 T cell clones and the biological activity thereof.

Total RNA from T cell clone HC/2G-1 was purified from T cells using an RNeasy Mini Kit (Qiagen, Valencia, Calif., USA). Primers having a nucleotide sequence complementary to the 3' end of the coding sequences of TCR α and β chains were synthesized (Operon Technologies, Huntsville, Ala.) to make full-length cDNAs. The primers sequences were as follows: Cα (TCAGCTGGACCACAGCCGCAGC; SEQ ID NO: 9), Cβ1 (TCAGAAATCCTTTCTCTTGACCATG; SEQ ID NO: 10) and Cβ2 (CTAGCCTCTGGAATC-CTTTCTCTTG; SEQ ID NO: 11). RACE reaction was performed by using a SMART™ RACE cDNA Amplification Kit (Clontech, Mountain View, Calif.) following the manufacturer's protocol. The RACE cDNAs (~1 kb) were obtained with Cα and Cβ1 primers and then ligated into a pCR2.1 vector with a TA Cloning® Kit (Invitrogen Life Technologies). The sequences of HC/2G-1 TCR α and β chains are found herein as SEQ ID NOs: 1-4, wherein SEQ ID NO: 1 is the nucleotide sequence for TCR α, SEQ ID NO: 2 is the nucleotide sequence for TCR β, SEQ ID NO: 3 is the amino acid sequence for TCR α, and SEQ ID NO: 4 is the amino acid sequence for TCR β.

In vitro transcription of TCR α and β chains was performed using mMESSAGE mMACHINE ULTRA according to the manufacturer's recommendations (Ambion Inc., Austin, Tex., USA). The RNA was purified using the RNAeasy Mini Kit (Qiagen, Valencia, Calif., USA). The electroporation of mRNAs of TCR α and β chains was performed as described previously (Cohen et al., *J. Immunol.* 175: 5799-5808 (2005)). In summary, PBMC from allogeneic donors were stimulated with 50 ng/ml OKT3 for 3 days, washed, and resuspended in OPTI-MEM (Invitrogen Life Technologies) at 2.5×10$^7$/ml. PBMC (50-200 μl) were mixed with mRNA at various amounts and transferred to pre-chilled 2-mm cuvettes (Harvard Apparatus BTX, Holliston, Mass., USA). Electroporation was performed at 400V per 500 μs using an ECM830 Electro Square Wave Porator (Harvard Apparatus BTX). Following electroporation, the cells were transferred to fresh RPMI supplemented with 10% HS and 300 IU/ml IL-2, and incubated at 37° C.

Electroporated cells were analyzed for the expression of Vβ2 by flow cytometry. As shown in FIG. 4A, the electroporated cells expressed Vβ2, meaning that the cells expressed the HC/2G-1 TCR α and β mRNAs.

The activity of the electroporated cells was then analyzed by assaying IFN-γ secretion upon stimulation with renal tumors. Specifically, OKT-3 stimulated T cells electroporated with mRNAs of either the HC/2G-1 TCR α chain, HC/2G-1 TCR β chain, or both (2 μg each) were co-cultured with renal tumors overnight and tested for IFN-γ secretion. RCC#11 was used as a negative control. As shown in FIG. 4B, both TCR chains were required for TCR recognition of tumor cells.

T cells (1×10$^5$) electroporated with mRNAs (1-4 μg/10$^6$ cells) were co-cultured with renal tumors, as well as control cells overnight, and the supernatants were harvested and tested for IFN-γ secretion. HC/2G-1 T cell clones were included in the same assay as a positive control. As shown in FIG. 4C, allogeneic T cells electroporated with HC/2G-1 TCR mRNAs recognize a variety of renal tumors.

OKT-3 stimulated allogeneic PBMC, CD8+-enriched, and CD4+-enriched cells were electroporated with HC/2G-1 TCR mRNAs (2 µg/ml) and co-cultured with renal tumors overnight. The supernatants were harvested and tested for IFN-γ secretion. RCC#11, 293 Tc, and 624 Tc served as negative controls in the assay. The Vβ2 expression of OKT-3 stimulated PBL, CD8+-enriched, and CD4+-enriched cells were also assayed and compared to the expression of CD3, CD8, and CD4, respectively. As shown in FIG. 4D, the recognition of HC/2G-1 TCR to renal tumors was neither CD8- nor CD4-dependent.

This example demonstrated that allogeneic cells expressing the TCR of HC/2G-1 T cell clones can recognize a variety of RCC cells in a CD8- and CD4-independent manner.

Example 5

This example demonstrates a method of producing allogeneic PBMCs retrovirally transduced with nucleic acids encoding the TCR of HC/2G-1 T cell clones and the activity of the transduced cells.

HC/2G-1 TCR α and β chains were ligated into a pMSGV1 plasmid, which is a derivative of the murine stem cell virus-based splice-gag vector (pMSGV), as described in previous publications with some modifications (Cohen et al., 2005, supra). Briefly, TCR α and β chain cDNAs were amplified by PCR using the following pairs of oligonucleotide primers to introduce appropriate restriction enzyme sites for subcloning: TCR α forward 5'-TCTAGCCATGGCACTTTCTAGC-CTGC-3' (SEQ ID NO: 12) and reverse 5'-ATAGCGGC-CGCTCAGCTGGACCACAG-3' (SEQ ID NO: 13); TCR 13 primer forward 5'-ATCTACTCGAGATGCTGCTGCTTCT-GCTGCTGCTTCTG-3' (SEQ ID NO: 14) and reverse 5'-TCTGCAGAATTCGGCTTCAGAAATC-CTTTCTCTTG-3' (SEQ ID NO: 15). The vector was assembled by ligation of four DNA fragments: pMSGV1 (NcoI/EcoRI), TCR-α cDNA (NcoI/NotI), internal ribosomal entry site (IRES) (NotI/XhoI), and TCR-β cDNA (xhoI/EcoRI) (FIG. 5A).

To produce retrovirus, Phoenix Eco cells was transfected with 24 µg of pMSGV1-HC/2G-1 plasmid DNA using Lipofectamine 2000 (Invitrogen Life Technologies). Two days later, the supernatant was harvested and used to infect a PG13 packaging line. The PG13-transduced cells were then cloned by limiting dilution. The presence of TCR genes was verified by dot-blot assay. The biological activities of retrovirus were determined by infecting SupT1 with PG13 packaging clones and analyzed by flow cytometry.

Two days before retroviral transduction, PBMCs from allogeneic donors were stimulated with OKT-3 (50 ng/ml) and IL-2 (300 IU/ml). The stimulated cells were added to RetroNectin (Takara Bio Inc. Japan), subsequently added to retrovirus pre-coated 24-well plates at $5\times10^5$/ml, and incubated overnight at 37° C. in a 5% $CO_2$ incubator. The procedure was repeated twice and the cells were split as necessary to maintain a cell density between 0.5 and $2\times10^6$ cells/ml. The expression of Vβ2 of the TCR was assayed to determine the retroviral transduction efficiency.

Packaging cell line PG13 transduced with retroviral HC/2G-1 TCR was cloned by limiting dilution. Clone E8 was selected for the remaining experiments. OKT-3 stimulated PBMCs from 4 different donors were transduced with Clone E8 three times and tested for CD3 and Vβ2 expression by flow cytometry three days post-transduction. PBMCs without transduction were used as controls (not shown). As shown in FIG. 5B, TCR transduced-PBMCs expressed Vβ2, indicating that the transduced cells expressed the TCR of HC/2G-1 T cell clones.

Three days after transduction, TCR-transduced PBMC ($1\times10^5$/well) were co-cultured with renal tumors overnight and tested for IFN-γ secretion. GFP-transduced PBMC and HC/2G-1 ($1\times10^4$/well) served as negative and positive controls, respectively. As shown in FIG. 5C, PBMCs transduced with HC/2G-1 TCR recognized a variety of renal tumors.

CD8- and CD4-enriched cells were isolated from GFP- or TCR-transduced PBMCs. As shown in FIG. 5D, the recognition by HC/2G-1 TCR in TCR-transduced PBMCs was both CD8- and CD4-independent.

This example demonstrated that allogeneic PBMCs can be transduced to express the TCR of HC/2G-1 T cell clones and have activity that is similar to HC/2G-1.

Example 6

This example demonstrates a method of treating cancer in a patient.

Human TILs from the tumors of patients are expanded as described in Walter et al., *New England J. of Med.* 333: 1038-1044 (1995). Briefly, TIL are expanded in the rapid expansion protocol (REP) in the presence of OKT3 and allogeneic feeder PBMCs. On day 7, TIL are transduced by exposing cells to Retronectin-coated plus TCR vector-coated tissue culture plates and incubated on the plates overnight. The transduction is repeated on the following day in the same manner. Cells are then washed and maintained in CM supplemented with IL-2. Eight days later, cells are assayed for activity by co-incubating transduced cells ($1\times10^5$ cells per well of a flat-bottom 96 well plate) with $1\times10^5$ target cells (e.g., RCC cells). After 24 hours of incubation, supernatants are harvested and IFNγ is quantified by ELISA capture assay. The cells which release >200 pg/ml IFNγ against the appropriate target cells (e.g., RCC cells) are further expanded. FACS analysis for the specific Vβ gene protein is used to detect the transduced genetic material. The level of the transduced Vβ gene expression is expected to be >5% prior to cell infusion.

Active transduced TIL are further expanded by stimulating with OKT3, allogeneic feeder cells, and IL-2. These components are mixed together in a tissue culture flask and transduced TIL are added to the flask.

PBLs are isolated by leukopheresis. Lymphocytes are separated by centrifugation on a Ficoll cushion, washed in HBSS, then resuspended at a concentration of $1\times10^6$ cells/ml in T cell culture medium supplemented with 50 ng/ml OKT3, 300 IU/ml IL-2, and 5% human AB serum. After 2 days of culture, cells are collected, resuspended in fresh medium without OKT3, plated onto tissue culture plates pre-coated with Retronectin and the TCR retroviral vectors, and incubated overnight. The transduction is repeated the following day. Two days after this last transduction, the PBLs are assayed for the presence of Vβ gene expression and for activity as described above. At least 10% of more of the transduced cells are expected to express the Vβ gene. Also, transduced cells are expected to release >200 pg/ml IFNγ against the appropriate target cells.

The active and transduced TIL or PBLs are infused into RCC patients by intravenous infusion plus IV-IL-2 (720,000 IU/kg q8h for a maximum of 15 doses). Patients' blood samples are obtained and are tested for T cells expressing the Vβ gene at 1, 3, 6, and 12 months after infusion. RCC tumor regression is expected to ensue.

This example demonstrates a method of treating renal cell carcinoma in a patient.

Example 7

This example demonstrates that transducing cells with a nucleic acid encoding a substituted TCR comprising SEQ ID NO:23, wherein Xaa117 is Phe and Xaa119 is Ser, secrete higher levels of IFN-γ than cells that are transduced with a nucleic acid encoding an unsubstituted TCR.

The activity of HC/2G-1 T cell clones (HC/2G-1) and PBL transduced with nucleic acids encoding GFP, unsubstituted TCR (WT) (including SEQ ID NO:3), TCR including SEQ ID NO:23, wherein Xaa117 is Trp and Xaa119 is Ser (109Y-W), and TCR including SEQ ID NO:23, wherein Xaa117 is Phe and Xaa119 is Ser (109 Y-F) is evaluated by assaying IFN-γ secretion upon stimulation with renal tumors. The transduced cells are cultured alone (medium) or co-cultured with renal tumor cells overnight (RCC Nos. 1, 6, 7, 8, and 10, or co-cultured with control cells RCC No. 11 and melanoma cells 624mel, 938mel, and 1300mel) and tested for IFN-γ secretion.

As shown in FIG. 6A, the cells that are transduced with a nucleic acid encoding a substituted TCR including SEQ ID NO:23, wherein Xaa117 is Phe and Xaa119 is Ser (109Y-F), secrete higher levels of IFN-γ than HC/2G-1 T cell clones (HC/2G-1) or the cells that are transduced with a nucleic acid encoding GFP, an unsubstituted TCR (WT) or a TCR including SEQ ID NO:23, wherein Xaa117 is Trp and Xaa119 is Ser (109Y-W).

This example demonstrates that cells that are transduced with a nucleic acid encoding a substituted TCR including SEQ ID NO:23, wherein Xaa117 is Phe and Xaa119 is Ser, secrete higher levels of IFN-γ than cells that are transduced with a nucleic acid encoding an unsubstituted TCR or a TCR including SEQ ID NO:23, wherein Xaa117 is Trp and Xaa119 is Ser (109Y-W).

Example 8

This example demonstrates that cells that are transduced with a nucleic acid encoding a substituted TCR including SEQ ID NO:22, wherein Xaa119 is Lys, secrete higher levels of IFN-γ than cells that are transduced with a nucleic acid encoding an unsubstituted TCR.

The activity of HC/2G-1 T cell clones (HC/2G-1) and PBL that are transduced with nucleic acids encoding GFP, unsubstituted TCR (WT) (including SEQ ID NO:3), TCR including SEQ ID NO:22, wherein Xaa119 is Lys (112S-K), TCR including SEQ ID NO:22, wherein Xaa119 is Asn (112S-N), TCR including SEQ ID NO:22, wherein Xaa119 is Leu (112S-L), TCR including SEQ ID NO:22, wherein Xaa119 is Tyr (112S-Y), TCR including SEQ ID NO:22, wherein Xaa119 is Thr (112S-T), and TCR including SEQ ID NO:22, wherein Xaa119 is Gly (112S-G) is evaluated by assaying IFN-γ secretion upon stimulation with renal tumors. The transduced cells are cultured alone (medium), co-cultured with renal tumor cells overnight (RCC Nos. 1, 6, 7, 8, and 10, or co-cultured with control cells RCC No. 11 and melanoma cells 624mel, 938mel, and 1300mel) and tested for IFN-γ secretion.

As shown in FIG. 6B, the cells that are transduced with a nucleic acid encoding a substituted TCR including SEQ ID NO:22, wherein Xaa119 is Lys (112S-K), secrete higher levels of IFN-γ than HC/2G-1 T cell clones (HC/2G-1) or the cells that are transduced with GFP, a nucleic acid encoding an unsubstituted TCR (WT) or a TCR including SEQ ID NO:22, wherein Xaa119 is Asn (112S-N), TCR including SEQ ID NO:22, wherein Xaa119 is Leu (112S-L), TCR including SEQ ID NO:22, wherein Xaa119 is Tyr (112S-Y), TCR including SEQ ID NO:22, wherein Xaa119 is Thr (112S-T), or a TCR including SEQ ID NO:22, wherein Xaa119 is Gly (112S-G).

This example demonstrates that cells that are transduced with a nucleic acid encoding a substituted TCR including SEQ ID NO:22, wherein Xaa119 is Lys, secrete higher levels of IFN-γ than cells that are transduced with a nucleic acid encoding an unsubstituted TCR or a TCR including SEQ ID NO:22, wherein Xaa119 is Asn (112S-N), TCR including SEQ ID NO:22, wherein Xaa119 is Leu (112S-L), TCR including SEQ ID NO:22, wherein Xaa119 is Tyr (112S-Y), TCR including SEQ ID NO:22, wherein Xaa119 is Thr (112S-T), or a TCR including SEQ ID NO:22, wherein Xaa119 is Gly (112S-G).

Example 9

This example demonstrates that cells that are transduced with a nucleic acid encoding a substituted TCR including SEQ ID NO:23, wherein Xaa117 is Phe and Xaa119 is Lys, secrete higher levels of IFN-γ than cells that are transduced with a nucleic acid encoding an unsubstituted TCR.

The activity of HC/2G-1 T cell clones (2G-12), untransduced PBL, and PBL that are transduced with nucleic acids encoding GFP, unsubstituted TCR (WT) (including SEQ ID NO:3), TCR including SEQ ID NO:22, wherein Xaa119 is Ala (A:aa112 S-A), TCR including SEQ ID NO:23, wherein Xaa117 is Phe and Xaa119 is Ser (A:aa109Y-F), TCR including SEQ ID NO:22, wherein Xaa119 is Lys (A:aa112 S-K), TCR including SEQ ID NO:23, wherein Xaa117 is Phe and Xaa119 is Ala (A:aa109 Y-F/aa112 S-A), TCR including SEQ ID NO:23, wherein Xaa117 is Phe and Xaa119 is Lys (A:aa109 Y-F/aa112 S-K), is evaluated by assaying IFN-γ secretion upon stimulation with renal tumors. The transduced cells are cultured alone (medium), co-cultured with renal tumor cells overnight (RCC Nos. 1, 6, 7, 8, and 10, or co-cultured with control cells RCC No. 11 and melanoma cells 624mel, 938mel, and 1300mel) and tested for IFN-γ secretion.

As shown in FIG. 6C, the cells that are transduced with a nucleic acid encoding a substituted TCR including SEQ ID NO:22, wherein Xaa119 is Ala (A:aa112 S-A), TCR including SEQ ID NO:23, wherein Xaa117 is Phe and Xaa119 is Ser (A:aa109 Y-F), TCR including SEQ ID NO:22, wherein Xaa119 is Lys (A:aa112 S-K), TCR including SEQ ID NO:23, wherein Xaa117 is Phe and Xaa119 is Ala (A:aa109 Y-F/aa112 S-A), TCR including SEQ ID NO:23, wherein Xaa117 is Phe and Xaa119 is Lys (A:aa109 Y-F/aa112 S-K) each secrete higher levels of IFN-γ than HC/2G-1 T cell clones (2G-12) or the cells that are transduced with GFP, or a nucleic acid encoding an unsubstituted TCR (WT).

This example demonstrates that cells transduced with a nucleic acid encoding a substituted TCR including SEQ ID NO:22, wherein Xaa119 is Ala (A:aa112 S-A), TCR including SEQ ID NO:23, wherein Xaa117 is Phe and Xaa119 is Ser (A:aa109 Y-F), TCR including SEQ ID NO:22, wherein Xaa119 is Lys (A:aa112 S-K), TCR including SEQ ID NO:23, wherein Xaa117 is Phe and Xaa119 is Ala (A:aa109 Y-F/aa112 S-A), TCR including SEQ ID NO:23, wherein Xaa117 is Phe and Xaa119 is Lys (A:aa109 Y-F/aa112 S-K) each secrete higher levels of IFN-γ than HC/2G-1 T cell clones (2G-12) or the cells that are transduced with GFP, or a nucleic acid encoding an unsubstituted TCR (WT), secrete higher levels of IFN-γ than cells that are transduced with a nucleic acid encoding an unsubstituted TCR (WT) or the HC/2G-1 T cell clones (2G-12).

Example 10

This example demonstrates that the activity, e.g., IFN-γ, of HC/2G-1 T cell clones is mediated by the cell surface protein TRAIL.

Autologous RCC cells (RCC #1) and allogeneic RCC cells (RCC #6 and #8) are co-cultured with HC/2G-1 T cells in the presence of anti-TRAIL antibody or in the absence of anti-TRAIL antibody. As a control, MART-1-reactive CTL cells are co-cultured with HC/2G-1 T cells in the presence of anti-TRAIL antibody or in the absence of anti-TRAIL antibody. The supernatants are harvested and assayed for IFN-γ concentration.

As shown in FIG. 7, the reactivity of HC/2G-1 T cell clones is blocked by anti-TRAIL antibodies and is not blocked in the absence of anti-TRAIL antibodies. In contrast, the anti-TRAIL antibody does not affect the activity of HC/2G-1 T cells stimulated with MART-1 reactive CTL control cells, as shown in FIG. 7.

This example demonstrates that the activity, e.g., IFN-γ, of the T cell clone HC/2G-1 is mediated by TRAIL.

Example 11

This example demonstrates that the activity, e.g., IFN-γ, of HC/2G-1 T cell clones is enhanced by the addition of recombinant soluble TRAIL protein.

HC/2G-1 T cells are cultured alone (medium) or in the presence of autologous (#1) and allogeneic (#5, 6, 8, 9, or 11) RCC cells, allogeneic EBV-B cells (EBV-B #3, 5, 6, 8, 11), or melanoma cells (624mel cells, 938mel cells, 1300mel cells, ANmel cells, RYmel cells, or SK23 cells), in the presence or absence of exogenous soluble TRAIL. The supernatants are harvested and assayed for IFN-γ concentration.

As shown in FIG. 8, exogenous TRAIL enhances the reactivity of HC/2G-1 T cell clones toward the RCC cells.

This example demonstrates that exogenous soluble TRAIL enhances the activity, e.g., IFN-γ, of the T cell clone HC/2G-1.

Example 12

This example demonstrates that HC/2G-1 T cells are activated (as measured by, e.g., IFN-γ, secretion) by HEK 293 cells that express the TRAIL receptor TRAIL-R1, but not by HEK 293 cells that express GFP or the TRAIL receptor TRAIL-R2.

HEK 293 cells are transduced to express TRAIL-R1 (DR4), TRAIL-R2 (DR5) or GFP, and co-cultured with HC/2G-1 T cells. The supernatants are harvested and assayed for IFN-γ concentration.

As shown in FIG. 9, HC/2G-1 T cells are activated by HEK 293 cells that express TRAIL-R1, but not by HEK 293 cells that express GFP or TRAIL-R2.

This example demonstrates that HC/2G-1 T cells are activated by target cells expressing the TRAIL receptor TRAIL-R1 as measured by, e.g., IFN-γ, secretion.

Example 13

This example demonstrates that HC/2G-1 T cells are activated by CHO cells that express TRAIL-R1 and CD58, as measured by, e.g., IFN-γ, secretion.

HC/2G-1 T cells are co-cultured with CHO cells that are transduced with GFP, TRAIL-R1, CD58, TRAIL-R2, co-transduced with both TRAIL-R1 and CD58, or co-transduced with TRAIL-R2 and CD58 in the presence of anti-TCR Ab or in the absence of antibody. The supernatants are harvested and assayed for IFN-γ concentration.

As shown in FIG. 10, HC/2G-1 T-cell clones are activated upon stimulation with CHO cells that are co-transduced with both TRAIL-R1 and CD58.

This example demonstrates that TRAIL-R1 and CD58, together, stimulate the activation of HC/2G-1 T-cell clones as measured by, e.g., IFN-γ, secretion.

Example 14

This example demonstrates that the cytoplasmic portion of TRAIL-R1 does not participate in target recognition by HC/2G-1 T-cell clones as measured by, e.g., IFN-γ, secretion.

HC/2G-1 T-cell clones are co-cultured with CHO/CD58 cells transduced with pME vector constructs including TRAIL-R1 truncations. The truncations include: the extracellular and intracellular (including transmembrane domain (TM) and death domain (DD)) portions (pME TRAIL-R1 66-1472), the extracellular portion and a part of the intracellular portion (including transmembrane domain (TM) and death domain (DD)) (pME TRAIL-R1 66-1400), the extracellular portion, TM domain, and a part of the intracellular portion, but lacking the DD domain (pME TRAIL-R1 66-1199), the extracellular portion but lacking the intracellular portion (i.e., lacking both the transmembrane domain (TM) and death domain (DD)) portions (pME TRAIL-R1 66-869), and including the extracellular portion but lacking the entire intracellular portion (pME TRAIL-R1 66-782), or pME GFP. The supernatants are harvested and assayed for IFN-γ concentration.

As shown in FIG. 11, TRAIL-R1 truncations lacking all or a portion of the intracellular portions (e.g., lacking DD) do not prevent the activation of the HC/2G-1 T-cell clones. In contrast, TRAIL-R1 truncations lacking the TM do prevent the activation of HC/2G-1 T-cell clones.

This example demonstrates that the cytoplasmic portion of TRAIL-R1 does not participate in target recognition by HC/2G-1 T-cell clones as measured by, e.g., IFN-γ, secretion.

Example 15

This example demonstrates that TRAIL-R1, anti-CD2, and soluble TRAIL, together, stimulate the activation of HC/2G-1 T-cell clones as measured by, e.g., IFN-γ, secretion.

A plate is coated with one or both of recombinant TRAIL-R1-Fc and anti-CD2 antibody with or without loading recombinant soluble TRAIL protein onto TRAIL-R1. HC/2G-1 T-cell clones are cultured on the plate or with RCC#6 (as a positive control).

As shown in FIG. 12, HC/2G-1 T-cell clones are stimulated in the co-presence of soluble TRAIL, plate-bound TRAIL-R1, and plate-bound anti-CD2 antibody.

This example demonstrates that HC/2G-1 T-cell clones are activated in the co-presence of TRAIL-R1, anti-CD2, and soluble TRAIL as measured by, e.g., IFN-γ, secretion.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified TCR comprising the amino acid sequences of SEQ ID NOs: 3 and 4.

2. An isolated or purified protein comprising a first polypeptide chain comprising the amino acid sequence of SEQ ID NO: 3 and a second polypeptide chain comprising the amino acid sequence of SEQ ID NO: 4.

3. An isolated or purified nucleic acid comprising a nucleotide sequence encoding the TCR of claim 1.

4. A pharmaceutical composition comprising the TCR of claim 1 and a pharmaceutically acceptable carrier.

5. An isolated or purified TCR comprising SEQ ID NO: 4 and an amino acid sequence selected from the group consisting of
   a) SEQ ID NO: 22, wherein Xaa119 is selected from the group consisting of Lys and Ala; and
   b) SEQ ID NO: 23, wherein Xaa117 is Phe and Xaa119 is selected from the group consisting of Lys, Ala, and Ser.

6. An isolated or purified polypeptide comprising SEQ ID NO: 4 and an amino acid sequence selected from the group consisting of
   a) SEQ ID NO: 22, wherein Xaa119 is selected from the group consisting of Lys and Ala; and
   b) SEQ ID NO: 23, wherein Xaa117 is Phe and Xaa119 is selected from the group consisting of Lys, Ala, and Ser.

7. An isolated or purified protein comprising at least one of the polypeptides of claim 6.

8. An isolated or purified protein comprising first and second polypeptide chains, wherein the first polypeptide chain comprises an amino acid sequence selected from the group consisting of
   a) SEQ ID NO: 22, wherein Xaa119 is selected from the group consisting of Lys and Ala; and
   b) SEQ ID NO: 23, wherein Xaa117 is Phe and Xaa119 is selected from the group consisting of Lys, Ala, and Ser;
   and the second polypeptide chain comprises SEQ ID NO: 4.

9. An isolated or purified nucleic acid comprising a nucleotide sequence encoding the TCR of claim 5.

10. A pharmaceutical composition comprising the TCR of claim 5, and a pharmaceutically acceptable carrier.

* * * * *